United States Patent [19]
Errico et al.

[11] Patent Number: 5,688,273
[45] Date of Patent: Nov. 18, 1997

[54] SPINAL IMPLANT APPARATUS HAVING A SINGLE CENTRAL ROD AND PLOW HOOKS

[75] Inventors: Joseph P. Errico, Far Hills; Thomas J. Errico, Summit; James D. Ralph, Oakland, all of N.J.

[73] Assignee: Fastenetix, LLC., Summit, N.J.

[21] Appl. No.: 547,105

[22] Filed: Oct. 23, 1995

[51] Int. Cl.⁶ .................................................. A61B 17/70
[52] U.S. Cl. .................................................. 606/61; 606/72
[58] Field of Search .................................. 606/61, 60, 69, 606/70, 71, 72, 73; 623/17

[56] References Cited

U.S. PATENT DOCUMENTS

| | | |
|---|---|---|
| 4,805,602 | 2/1989 | Puno et al. |
| 4,946,458 | 8/1990 | Harms et al. ............ 606/61 |
| 4,987,892 | 1/1991 | Krag et al. ............ 606/61 |
| 5,005,562 | 4/1991 | Cotrel. |
| 5,176,680 | 1/1993 | Vignaud et al. ............ 606/61 |
| 5,190,543 | 3/1993 | Schlapfer ............ 606/61 |
| 5,207,678 | 5/1993 | Harms et al. ............ 606/61 |
| 5,217,497 | 6/1993 | Mehdian ............ 623/17 |
| 5,261,909 | 11/1993 | Sutterlin et al. ............ 606/61 |
| 5,261,912 | 11/1993 | Frigg ............ 606/61 |
| 5,306,275 | 4/1994 | Bryan ............ 606/61 |
| 5,360,431 | 11/1994 | Puno et al. ............ 606/72 |

Primary Examiner—Guy V. Tucker
Attorney, Agent, or Firm—Joseph P. Errico, Esq.

[57] ABSTRACT

A hook and rod apparatus for implantation and fixation to the centerline of the spine, wherein the rod provides for immobilization of the spine via its inherent rigidity. The hook elements are designed to be mounted at the arched portion of the lamina. In a first plow shaped variation, the blade portion of the hook is an arched surface which seats under the arched surface of the lamina. In a second claw shaped variation, the blade portion includes a bifurcated conformation having a pair of offset flat extending members which are offset so as to seat under the angled portions of the lamina which are directly laterally disposed relative to the arched center of the lamina. The rod coupling features of the hooks may further be polyaxial by virtue of separate coupling elements which may be mounted to the blade portion, for example on a semi-spherical head portion thereof. In the alternative, the blade portion may have a contractible recess formed in a top thereof, for receiving and locking to a shaft of body portion at a variety of heights. The rod receiving features of the hook may include both the polyaxial and height variability natures of both of the previous hooks by having a shaft portion which has a semi-spherical head onto which the coupling element is mounted.

6 Claims, 19 Drawing Sheets

5,688,273

SPINAL IMPLANT APPARATUS HAVING A SINGLE CENTRAL ROD AND PLOW HOOKS

BACKGROUND OF THE INVENTION

1. Field of the Invention

This invention relates generally to a hook and rod implant apparatus for immobilization of the spinal column. More particularly, the present invention relates to an implant apparatus comprising hook devices for attaching to the posterior lamina at a central position thereon, and a single support rod, securely held by the hooks to form a single central axis implantation apparatus.

2. Discussion of the Prior Art

The bones and connective tissue of an adult human spinal column consists of an upper portion having more than 20 discrete bones, and a lower portion which consists of the sacral bone and the coccygeal bodies. The bones of the upper portion are generally similar in shape, as will be more fully described hereinbelow with respect to FIGS. 1, 2 and 3. Despite their similar shape, however, they do vary substantially in size in accordance with their individual position along the column and are, therefore, anatomically categorized as being members of one of three classifications: cervical, thoracic, or lumbar. The cervical portion, which comprises the top of the spine, up to the base of the skull, includes the first 7 vertebrae. The intermediate 12 bones are the thoracic vertebrae, and connect to the 5 lumbar vertebrae.

The lower portion of the spinal column, which extends into the hip region is primarily comprised of the sacral bone. This bone is unlike the other bones of the spinal column, in both shape and size. In fact, at birth humans have five distinct sacral bones which begin to fuse together during childhood, and by adulthood have fully combined. For the purpose of describing this invention, however, the sacral bone shall be referred to as distinct from the spinal column; the spinal column, therefore, comprising for the purposes of this description, only the cervical, thoracic, and lumbar vertebrae.

The bones of the upper portion vary in size, but are each similarly coupled to the next by a tri-joint complex. The tri-joint complex consists of an anterior disc and the two posterior facet joints, the anterior discs of adjacent bones being cushioned by cartilage spacers referred to as intervertebral discs. Referring now to FIGS. 1, 2 and 3, top, lateral, and posterior views of a typical vertebral bones of the spinal column are shown. The spinal cord is housed in the central canal 10, protected from the posterior side by a shell of bone called the lamina 12. The lamina 12 has three large protrusions, two of these extend laterally from the side ends thereof and are referred to as the transverse processes 14. The third extends back and down from the center of the lamina and is called the spinous process 16. The lamina 12 defines an arched shape about the posterior of the spinal cord, the arched shape having lateral portions 13a,13b which are generally straight, and which meet beneath the spinous process at a curved surface 15.

The anterior portion of the spine comprises a set of generally cylindrically shaped bones which are stacked one on top of the other. These portions of the vertebrae are referred to as the vertebral bodies 20, and are each separated from the other by the intervertebral discs 22. Pedicles 24 are bone bridges which couple the anterior vertebral body 20 to the corresponding lamina 12 and posterior elements 14,16.

Referring specifically to FIG. 3, the stacking of vertebrae is shown from the posterior. From the posterior, each vertebra is coupled to the one above and below via facet joints 19 on either side of an opening into the spinal canal 10.

In its entirety, the spinal column is highly complex in that it houses and protects critical elements of the nervous system which have innumerable peripheral nerves and arterial and venous bodies in close proximity. In spite of these complexities, the spine is a highly flexible structure, capable of a high degree of curvature and twist through a wide range of motion. Genetic or developmental irregularities, trauma, chronic stress, tumors, and disease, however, can result in spinal pathologies which either limit this range of motion, or which threaten the critical elements of the nervous system housed within the spinal column. A variety of systems have been disclosed in the art which achieve this immobilization by implanting artificial assemblies in or on the spinal column.

These assemblies may be classified as anterior, posterior, or lateral implants. As the classification suggests, lateral and anterior assemblies are coupled to the anterior portion of the spine, which is the sequence of vertebral bodies. Posterior implants are attached to the back of the spinal column, generally by coupling to the pedicles via screws, or by means of hooks which attach under the lamina, and entering into the central canal. In either case, the implants generally comprise at least one (and usually a pair thereof) elongate support rod element which is coupled to the screws or hooks to immobilize several sequential vertebrae, for example to hold them stable so that the adjacent bones may be fused with bone graft. The prior co-pending application, U.S. Ser. No. 08/502,285, of which this application is a continuation-in-part, discloses novel devices which provide significantly superior performance for such implants which comprise screws for coupling to the pedicles. Inasmuch as the pedicles are disposed laterally with respect to the posterior profile of the column of vertebrae, the rods of such screw systems have universally been disposed to the sides of the central axis of the spine, lateral to the axis formed by the spinous processes. As set forth more fully hereinbelow, the disposition of the rods in the natural site for desired bone fusion, limited bone graft can be achieved. Maximal posterior bone fusion is desired for all immobilizations of such portions of the spine, and therefore, the placement of the rod in the best site for such bone growth is a drawback of lateral systems.

Hook and rod assemblies however, have not provided any superior access to the lateral portions of the posterior surfaces of the spine. Generally hook and rod assemblies of the prior art have included a plurality of hooks having rounded blade portions which are inserted posteriorly under the straight portion of the lamina between the transverse process and the spinous process (off the center line of the spine). The hooks include upper body portions to which the support rod is coupled.

Referring now to FIGS. 4 and 5, U.S. Pat. No. 5,005,562 to Cotrel teaches such a hook and rod apparatus which includes a pair of rods 30a,30b, which are coupled to hooks 32a,32b and 34a,34b. Upper hooks 32a,32b are disposed such that the blade portions are directed downward, hooking the straight (side) portion 13a,13b of the lamina 12 which is sequentially below them. Lower hooks 34a,34b are disposed in the opposite orientation, so that the blade portions thereof are directed upward relative to the axis of the spine. It is understood that the rods 30a,30b are also coupled to pedicle screws 36a–36d. The rods 30a,30b hold the hooks 32a–b, 34a–b to the lamina 12, preventing their movement out from beneath their respective lamina 12 by virtue of tensile rigidity in the rod. In addition, the rods 30a,30b are further stabilized by cross link devices 38a,38b. It is clear from FIG.

4 that there is little free space to place bone graft material, and in fact where such bone graft may ultimately grow is precisely where the implant is positioned, thereby risking difficulty of removal if long term post-operative problems necessitate removal of repair of the apparatus.

FIG. 5 illustrates one specific type of hook, the ones disclosed by U.S. No. Patent 5,005,562. These hooks have a blade portion, including a flat extending member 51 which is designed to fit snugly to the undersides of the flat portions 13a,13b of the lamina 12 which is next to the transverse processes (on either side of the spinous process). This hook further includes an integrally formed rod receiving body 52, which extends upwardly from the top of the blade portion 55. The rod receiving body 52 comprises a generally cylindrically shaped portion 54 having a vertical slot 58 formed in the top thereof for receiving the rod 30a or 30b. This rod is secured in the slot 58 by a threaded plug 56.

In addition to the disadvantages of the laterally disposed rod apparatuses, with respect to the availability of free space in which to introduce bone graft material, it has been identified that hooks having flat extending members which are disposed under the flat portion of the lamina 13a,13b may cause undue stress concentrations in the laminar bone. This is in part due to the location of the blade, the narrowness of the blade, as well as the torquing which the lateral offset implies. In addition, it is a function of the relative thinness of the lamina 12 at these sites.

Further, it has been found that considerable difficulty may be associated with inserting hooks under sequential lamina along a misaligned curvature while simultaneously exactly positioning their rod receiving portions thereof such that they are aligned so that the rod can be passed therethrough without distorting, tilting, rotating, or exerting undesired translational forces on the hooks. Correction of this difficulty requires the time consuming and difficult task of reshaping the rods or repositioning the hooks, each of which is understood to require considerably longer operating time, which is known to increase the incidence of complications associated with surgery. Often such alignments with such fixed body hooks cannot be satisfactorily achieved, and the entire instrumentationing effort has to be altered to utilizing screws. Any such time consuming efforts which afflict the implantation of a single rod assembly is understandably amplified with the necessity of implanting a parallel apparatus on the opposing lateral extent of the posterior of the spinal column.

It is, therefore, the principal object of the present invention to provide a single center axis hook and rod implant system to maximize desirable area for bone grafting purposes.

It is also a principal object of the present invention to eliminate the need for a second parallel apparatus to be implanted to stabilize and immobilize sequential vertebrae.

It is, relatedly, an object of the present invention to provide a simplified implantation apparatus which reduces the amount of operative time necessary for proper introduction thereof.

It is still further an object of the present invention to provide an implant apparatus which reduces the point stress loads on the laminar bones of the spine.

It is another principal object of the present invention to provide a lamina hook which may be utilized in accordance with the above objects.

It is relatedly an object of the present invention to provide a lamina hook having a rod coupling body which provides a polyaxial freedom of implantation angulation with respect to rod reception.

Accordingly it is also an object of the present invention to provide an assembly which is reliable, durable, and provides long term fixation support.

Other objects of the present invention not explicitly stated will be set forth and will be more clearly understood in conjunction with the descriptions of the preferred embodiments disclosed hereafter.

SUMMARY OF THE INVENTION

The preceding objects of the invention are achieved by the present invention which is a single axis, centerline, lamina hook and rod apparatus. The hook devices of this system may further include polyaxial and/or extending rod coupling bodies. More particularly, the hooks of this apparatus may comprise a blade portion having an extending member, or members, which seat under the lamina and are designed to fit snugly under the arched portion 15 thereof. The hooks are therefore designed to be seated beneath the thickest portion of the lamina, ensuring significant strength enhancement, and correspondingly reduced concern for laminar bone breakage at the hook-bone interface. These blades further provide self alignment to the hook relative to rotational forces which may be applied thereto.

In a first variation, this blade portion comprises a curved shape, herein referred to as the plow hook, having a single extending member which is curved in shape. The curve is approximated to the arch 15 at the center of the lamina. In a second variation, the blade portion includes a pair of extending members, each flat, but angled relative to one another so as to mutually seat against the undersides of the lamina on either side of the curved portion of the laminar arch 15. This second variation shall be herein referred to as the claw hook variation.

The implantation of such a device may require the removal of the spinous process, inasmuch as a preferred position of the rod receiving body portion of the hook is directly along the centerline of the spine (often defined by the sequence of spinous processes). It shall be understood that embodiments of this apparatus may be contemplated, some of which are herein disclosed, which do not require the removal of the spinous process, and which do include the capacity for a parallel rod to be implanted. It is, however, herein noted that the spinous process is not a structurally significant feature providing direct support to the spinal column. In fact, the spinous processes is often removed for use as bone graft material, or to provide increased potential bone graft sites in instances wherein there is such a reduction in alternative bone graft site due to the apparatuses implanted (which is precisely an advantage of the present invention).

In addition, this invention achieves the objects set forth above with respect to ease of alignment by providing polyaxial and/or extending rod coupling body portions. More specifically, in a first such embodiment, the hook comprises a ball shaped head. The body of the device comprises a separate coupling element mounted on the ball shaped (semi-spherical) head so that it is rotationally free prior to secure fixation of the rod thereto, and which is securely locked in a given angulation once the rod is received by the coupling element. The coupling element has a generally cylindrical main body portion, a locking ring, an external rod securing sleeve, and a top locking nut.

The coupling element may be conceptually divided into a lower socket portion, and an upper rod receiving portion. The lower socket portion is designed with an interior chamber having an opening at the bottom of the coupling element.

The interior chamber is provided for receiving therein the head of the blade portion such that the blade and the coupling element are held together, but prior to the securing of the rod to the intermediate portion, the blade and coupling element remain free to swing and rotate freely with respect to one another. The external surface of the socket portion includes at least one vertical slot which is provided so that the semi-spherical head, which has a major diameter which is larger than the opening in the bottom of the element may be received within the open volume therein. The at least one slot resiliently expands to receive the head and contracts into position once the head is fully inserted, therein inhibiting the head from being retracted.

The exterior of the lower portion of the coupling element, into which the head is inserted, tapers outward slightly toward the bottom of the element, therein having a slightly wider bottom diameter than at the top of the lower portion. A locking ring, having a diameter equal to or greater than the top of the lower portion, but less than the diameter of the bottom of the lower portion, is disposed initially about the top of the lower portion.

Subsequent to proper positioning of the blade portion of the hook under the corresponding arch of the desired lamina, the coupling of the rod to the coupling element (as set forth in more detail hereinbelow), and the setting of the proper angulation of the coupling element relative to the hook, the locking ring may be forced by a sufficient application of pressure downward along the exterior of the lower portion of the coupling element. The locking ring therein applies an inward force against the walls of the interior chamber, and the corresponding narrowing of the vertical slots thereof. Once fully driven downward the locking ring causes the coupling element to be securely locked relative to the blade portion of the hook.

The upper portion of the coupling element comprises a channel formed therein, wherein the rod is retained. More particularly, the upper portion comprises a pair of upwardly extending members, defining therebetween a vertical rod receiving channel. The outer surface of the upwardly extending members further include a threading which is ideally suited for receiving thereon a top locking nut. The locking ring on the lower portion is initially positioned so that the upper annular surface thereof extends vertically above the bottom of the channel, so that in its initial disposition in the channel, the rod seats on the locking ring. As the nut descends onto the coupling element to lock the rod in place, the rod is driven downward, causing the locking ring to descend along the exterior of the lower section, crush locking the head of the hook to the interior chamber of the coupling element.

More specifically, the downward movement of the rod within the channel, caused by the downward force of the nut, forces the locking ring downward along the tapered lower portion. Ultimately the inward radial force applied to the lower portion of the coupling element causes the at least one slot therein to close and for the head of the hook to be locked therewith. The rod, too, is then securely locked between the top of the locking ring and the nut, and is thereby prevented from axial or rotational movement.

An optional rod securing sleeve may also be provided for holding the rod in the channel and preventing it from moving relative thereto. The optional rod securing sleeve is generally cylindrical in shape, having a hollow center for sliding over the top of the coupling element. The bottom of the sleeve includes two opposing downwardly extending members; forming therebetween a second channel. The sleeve, therefore, has a conformation which resembles an upside down U-shape and cups the rod from above. Subsequent to the placement of the rod in the channel, the rod securing sleeve may be deposited on the coupling element such that the rod is positioned within the vertically aligned slots therein. The nut therefore seats against the top of the sleeve, the sleeve against the rod, and the rod against the locking ring.

In a second embodiment, the hook has a variable height extending body portion and a blade portion to which the variable height body portion may be coupled. More particularly, the blade portion comprises a body coupling end having a cylindrically shaped recess in the top thereof. The cylindrical recess is oriented to be generally perpendicular to the axis of the spine. The top of the cylindrically shaped recess comprises a slotted opening so as to be selectively contractible by an inwardly directed radial force. The external surface of the body coupling end, which includes the slots also includes a taper, for example a narrower top. This tapered portion further comprises an external threading so that a nut may be introduced onto the threading; the tightening of which causes the selective contraction of the top of the cylindrical recess.

In this second embodiment, the body of the device comprises a top loading coupling element which includes an elongate lower shaft portion. The shaft portion is designed to be slidably and rotationally mounted within the cylindrical recess so that prior to being locked into place by tightening the top of the recess to the shaft, the coupling element may be rotationally varied relative to the blade portion, and raised or lowered within the cylindrical recess and relative to the blade. In a preferred variation of this embodiment, the shaft portion is restrained against full removal from the recess in the blade portion by means of a mutual track feature, guide rails, or equivalent means.

The rod receiving upper portion of the coupling element has a channel therein, formed between a pair of upwardly extending members which are substantially similar to the upper portion of the coupling element described above. As above the rod may be locked in the channel by means of a top locking nut, or also with an optional rod securing sleeve. This rod receiving upper portion, therefore, is generally equivalent to the parallel features of the first embodiment, but for the lack of a locking ring. In this embodiment, application of the locking nut downward onto the rod crushes the rod to the bottom surface of the side recess in which it is mounted (as opposed to onto the top surface of a locking ring as in the first embodiment).

In a preferred variation of this second embodiment, however, the top of the rod receiving coupling element portion has a small threaded recess therein for receiving a threaded post for alignment and positioning prior to being locked into place.

The implantation of this second embodiment may begin with the positioning of the blade portion under the arched portion of the lamina. As stated above, in this proper position, the body mating end of the blade portion, and the cylindrical recess therein, are disposed above the lamina, oriented such that the recess is directed substantially posteriorly relative to the patient's spine, and generally transverse to the support rod to be coupled to the body portion.

Once in position, the surgeon may either insert the shaft of the coupling element into the recess to the appropriate depth, therein providing for the necessary length body, or, if the coupling element is pre-loaded in the recess and restrained from full withdrawal therefrom, simply raise the body out of the recess to the necessary extent. In either case, rotational adjustment of the shaft about the axis of insertion is also possible. A tightening nut is then introduced onto the threading at the slotted and tapered top of the recess, and is tightened by rotation thereof until the slots in the tapered portion narrow, thereby locking the shaft therein. The direction and disposition of the tightening nut prior to the locking step varies with the specific embodiment, however, for the purposes of this description, the tightening nut is introduced from above. (In an alternative variation, the tightening nut could be pre-mounted to the exterior surface of the body receiving recess, and engage the threading from below. In such an embodiment, the taper of the upper portion of the body receiving portion would widen toward the top so that engagement of the tightening nut could selectively contract the opening by rotationally translating upwards on the threading.)

Once the shaft has been positioned and locked in place, the support rod may be inserted into the channel of the rod receiving portion of the body, and the locking nut placed thereover. The final downward translation of the locking nut securely locks the rod within the recess via a crush-locking of the rod between the bottom of the nut and the curved bottom of the channel. In the variation having an optional rod securing sleeve, as above, the rod securing sleeve is introduced between the rod and the top locking nut to be crush locked to the rod by downward translation of the locking nut.

In a third embodiment, the hook assembly comprises a similar blade portion, tightening nut, and shaft portion of the body, however, the top of the shaft comprises a semi-spherical ball on which an independent rod coupling element is polyaxially mounted as set forth more fully hereinbelow. More specifically, this hook embodiment may be divided into a blade portion, and shaft portion, and a rod coupling element portion which is substantially equivalent to the polyaxial coupling element of the first embodiment. As above, the rod coupling element may be further conceptually divided into a lower socket portion, and an upper portion having a channel formed therein. The lower socket portion is designed with an interior chamber having an opening at the bottom of the coupling element. The interior chamber is provided for receiving therein the semi-spherical head of the shaft portion such that it and the coupling element are held together, but prior to the securing of the rod thereto, the coupling element remains free to swing and rotate freely with respect to the shaft and blade portions. The external surface of the socket portion includes at least one vertical slot which is provided so that the semi-spherical head, which has a major diameter which is larger than the opening in the bottom of the element may be received within the open volume therein. The at least one slot resiliently expands to receive the head and contracts into position once the head is fully inserted, therein inhibiting the head from being retracted.

The exterior of the lower portion of the coupling element, into which the head of the shaft is inserted, tapers outward slightly toward the bottom of the element, therein having a slightly wider bottom diameter than at the top of the lower portion. A locking ring, having a diameter equal to or greater than the top of the lower portion, but less than the diameter of the bottom of the lower portion, is disposed initially about the top of the lower portion.

Subsequent to proper positioning of the blade portion of the hook under the corresponding lamina, the shaft is locked to the blade portion as set forth with respect to the first polyaxial embodiment. The polyaxial coupling element is then angulated into the ideal position for receiving the support rod, and the locking ring may be forced by a sufficient application of pressure downward along the exterior of the lower socket portion thereof as set forth above in regards to the first embodiment.

The implantation of this embodiment begins as the first and second embodiments did, with the positioning of the blade portion relative to the lamina wherein the extending plow member is, or claw members are, placed under the lamina. The shaft portion, which comprises a semi-spherical head, is locked within the cylindrical recess by the application of the tightening nut.

The coupling element is then angulated as is required for the ideal capturing and securing of the rod in the channel thereof. Once the rod has been placed in the channel and is disposed on the top annular surface of the locking ring, the top locking nut is translated down onto the upwardly extending members to lock the rod in the channel and to force the locking ring downward to crush lock the semi-spherical head in the interior chamber of the lower portion of the coupling element.

In the variation in which the optional rod securing sleeve is utilized, the sleeve is placed over the coupling element and the top locking nut is then driven downward. This translation of the nut, which seats against the top surface of the sleeve, causes the rod and the locking ring to be forced downward as well. The downward translation of the locking ring causes the lower portion to lock to the semi-spherical head of the shaft.

It shall be understood that, as with the second embodiment, the coupling element may comprise an axial passageway, however in this embodiment the axial passageway extends from the top thereof through to the interior chamber, such that a threaded post may be utilized to engage a threaded recess in the semi-spherical head of the shaft portion, such that the shaft portion and the coupling element may be provided to the surgeon as initially polyaxially coupled parts. The axial passageway and the recess in the semi-spherical head may therefore be aligned so that the surgeon may raise and lower the shaft portion relative to the blade portion without disassembling the coupling element from the shaft.

Each of the above embodiments of the hook devices of the single center rod implant apparatus may include, in the alternative, two rod receiving body portions which are disposed to the sides of the spinous process (removed or not) so as to be compatible with two rods. Such an embodiment may be utilized, for example, wherein the rod receiving sites one side are used for initial alignment of the spine, and the opposing sides are used for final support.

BRIEF DESCRIPTION OF THE DRAWINGS

FIG. 10 is a side perspective view of the hook of

FIG. 7a, having a support rod secured therein with the top locking nut of FIGS. 8;

DETAILED DESCRIPTION OF THE PREFERRED EMBODIMENT

While the present invention will be described more fully hereinafter with reference to the accompanying drawings, in which particular embodiments and methods of implantation are shown, it is to be understood at the outset that persons skilled in the art may modify the invention herein described while achieving the functions and results of this invention. Accordingly, the descriptions which follow are to be understood as illustrative and exemplary of specific structures, aspects and features within the broad scope of the present invention and not as limiting of such broad scope.

Figure 2:
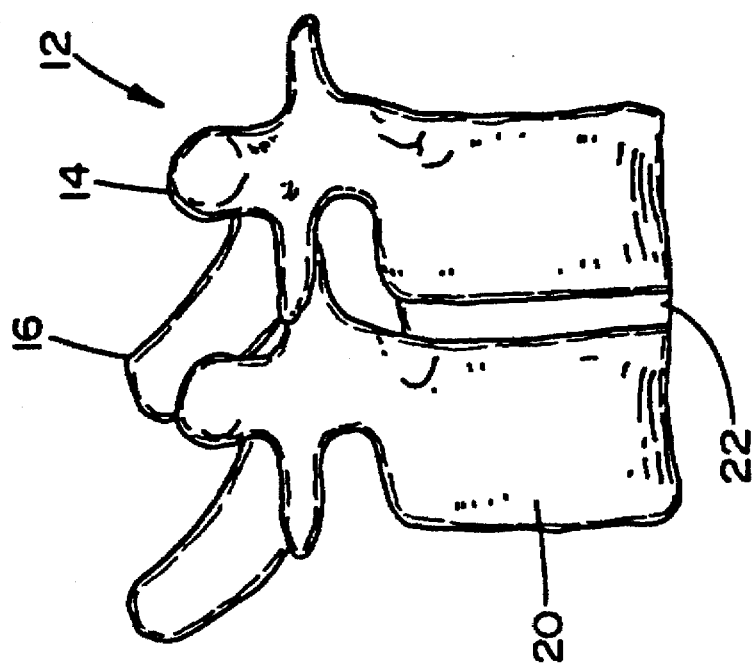
FIG. 2 is a side view of sequentially aligned vertebral bones, such as are found in the cervical, thoracic, or lumbar spine.
Figure 1:
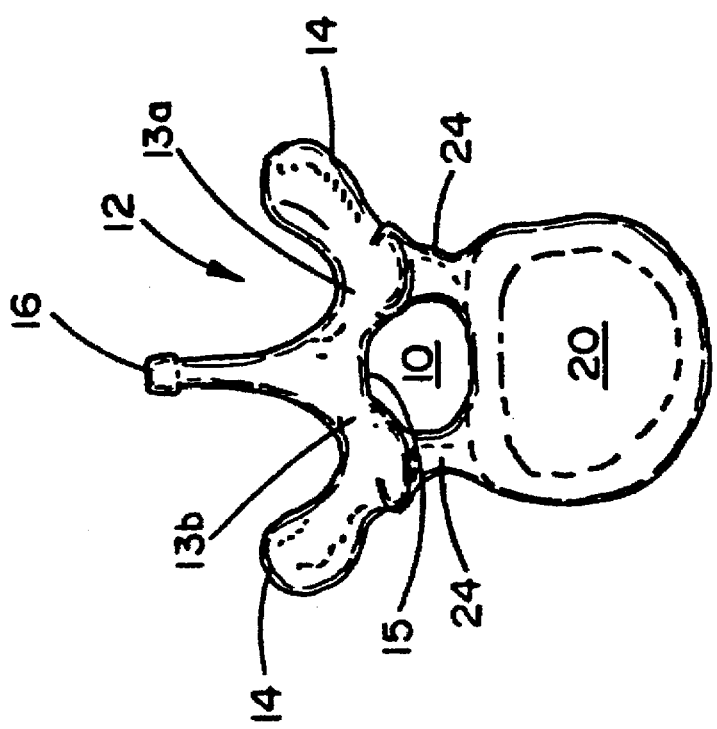
FIG. 1 is a top view of a vertebral bone characteristic of those of the cervical, thoracic, and lumbar spine.
Figure 3:
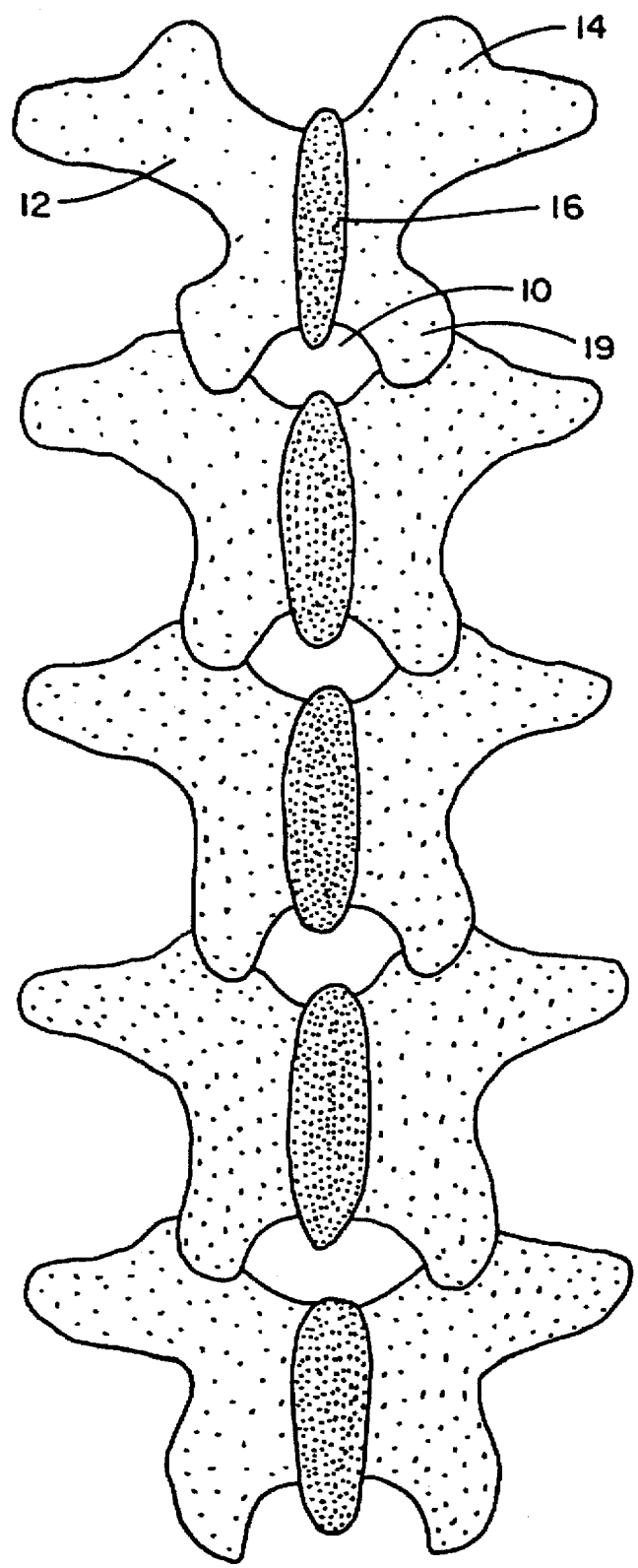
FIG. 3 is a posterior view of a sequence of vertebrae.
Figure 4:
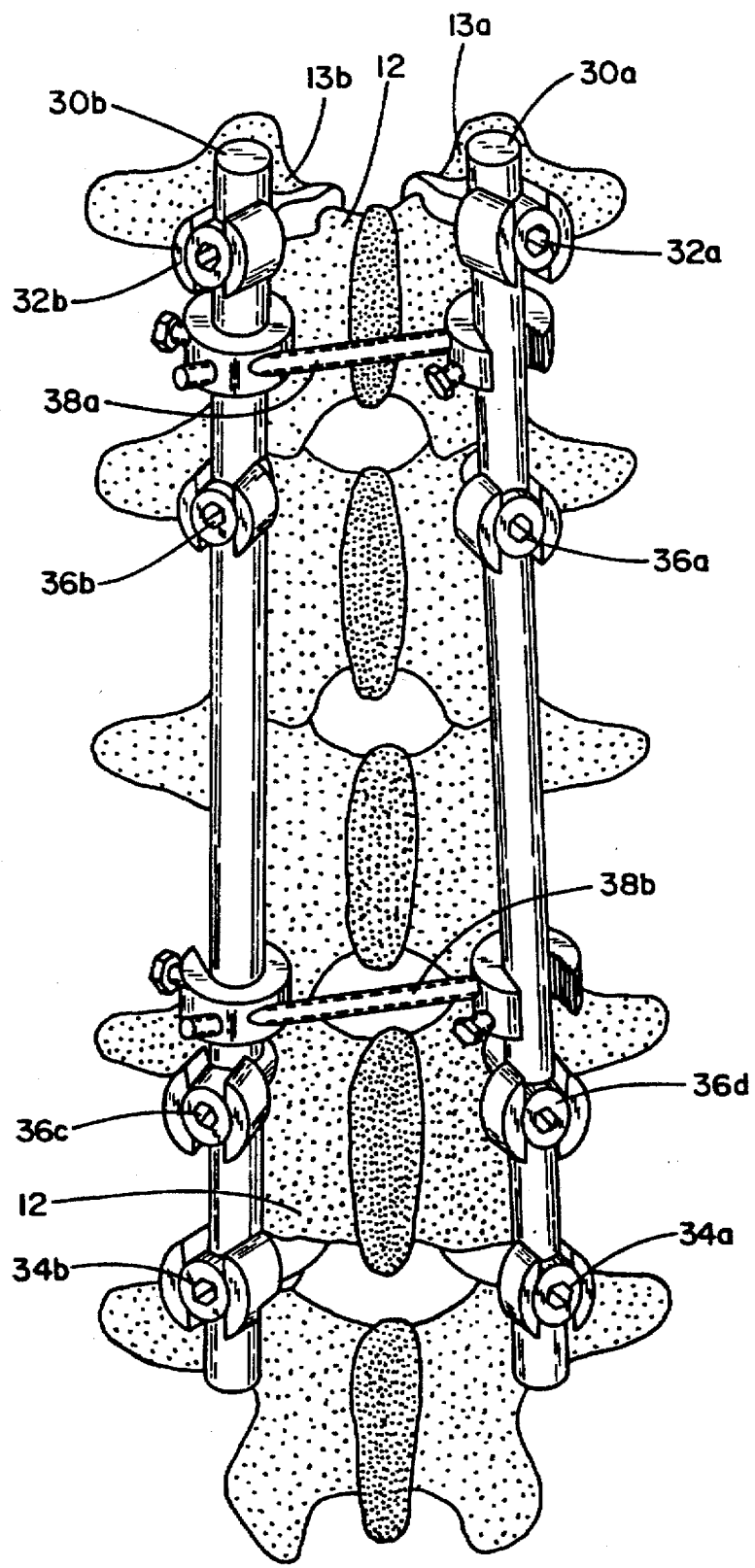
FIG. 4 is a posterior view of a hook, screw and rod system of the prior art.
Figure 5:
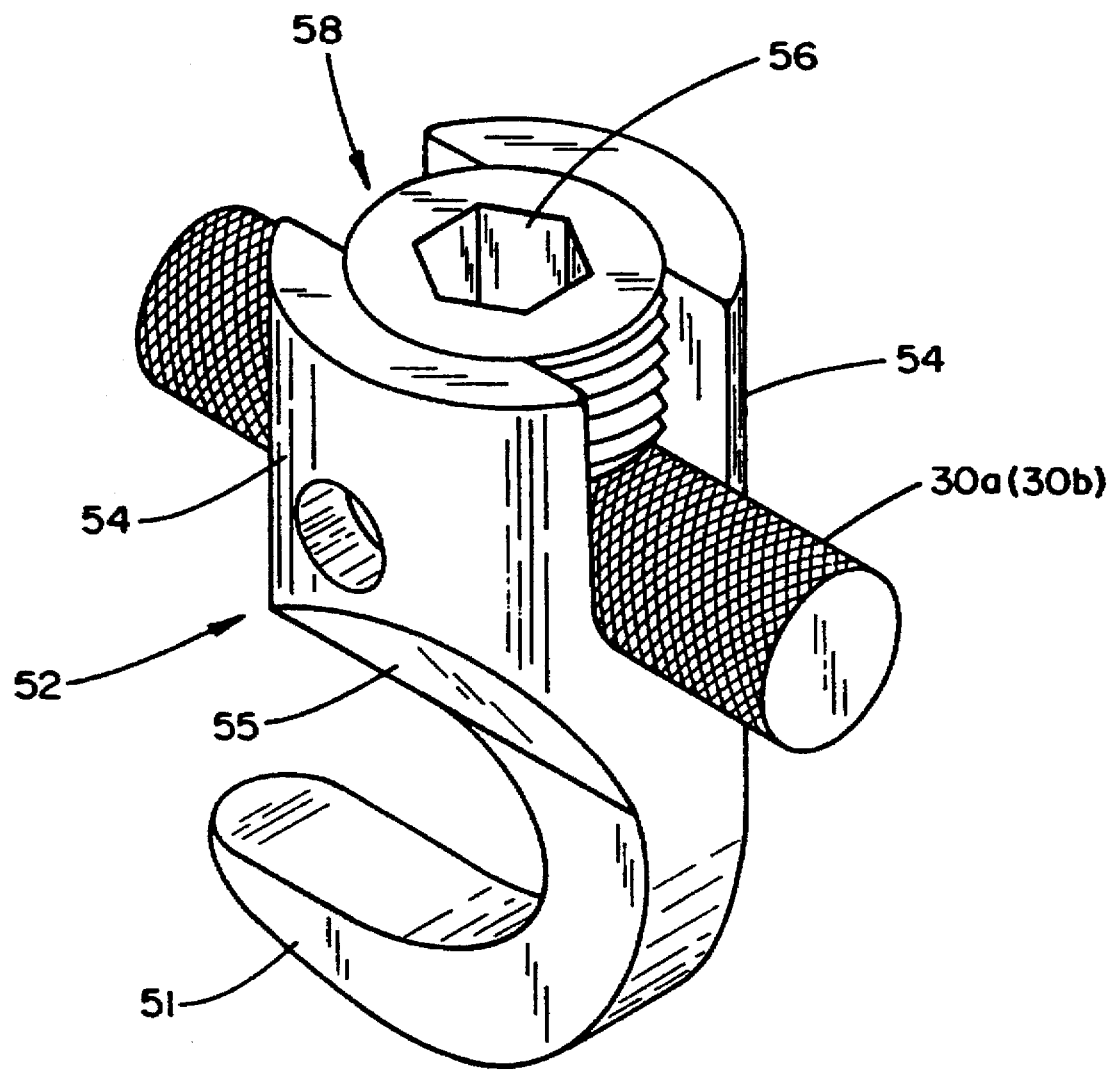
FIG. 5 is a side cross-sectional view of the hook device of the prior art apparatus of FIG. 4.
Figure 6:
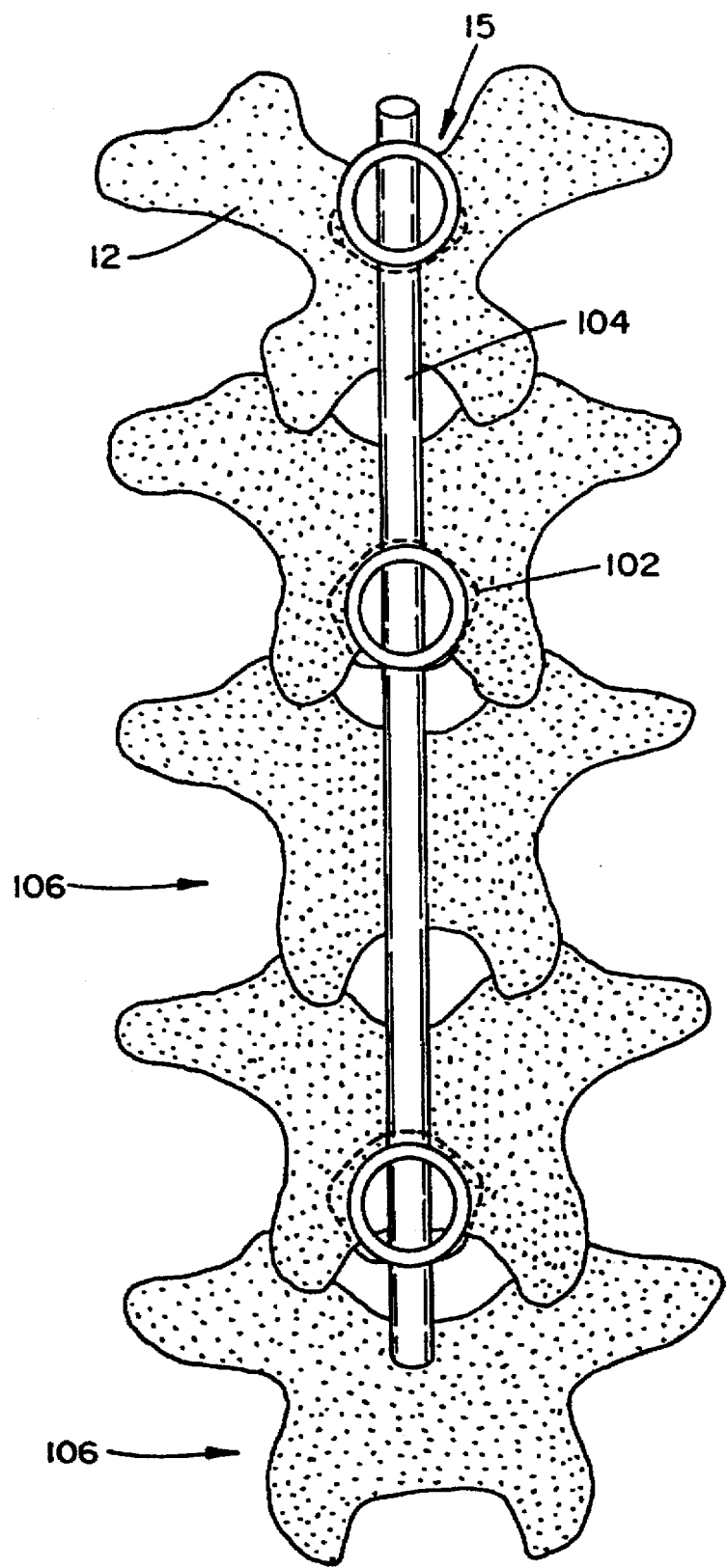
FIG. 6 is a posterior view of the hook and central rod apparatus of the present invention.

Referring now to FIG. 6, a posterior view of the centerline unitary rod and hook apparatus of the present invention is provided. As in FIG. 4, which illustrated a dual rod apparatus of the prior art, the present invention may be generally categorized as one which utilizes hooks to provide coupling of a rod to the spine, and which does so by being anchored under the lamina. More specifically, with respect to the present invention however, the hooks 102 are designed to be inserted under the arch of the lamina 12, wherein the undersurface of the bone forms a shallow inverted-V shape. Inasmuch as the rod 104 of this embodiment of the present invention is intended to extend downward along the centerline of the spine, it may be necessary to remove the spinous processes of the sequence of vertebrae along which the rod 104 is to extend. This includes vertebrae 106 to which the hooks 102 are not mounted, but which are disposed between vertebrae which are coupled by the apparatus, or which are adjacent to the sequence which is to be instrumented, and may therefore be effected by the presence of the rod. The removal of the spinous processes may be avoided if the disposition of the rod is to be above their profile, or if the rod receiving part of the hook is offset sufficiently for the rod to extend along them (see FIG. 22).

Figure 7A:
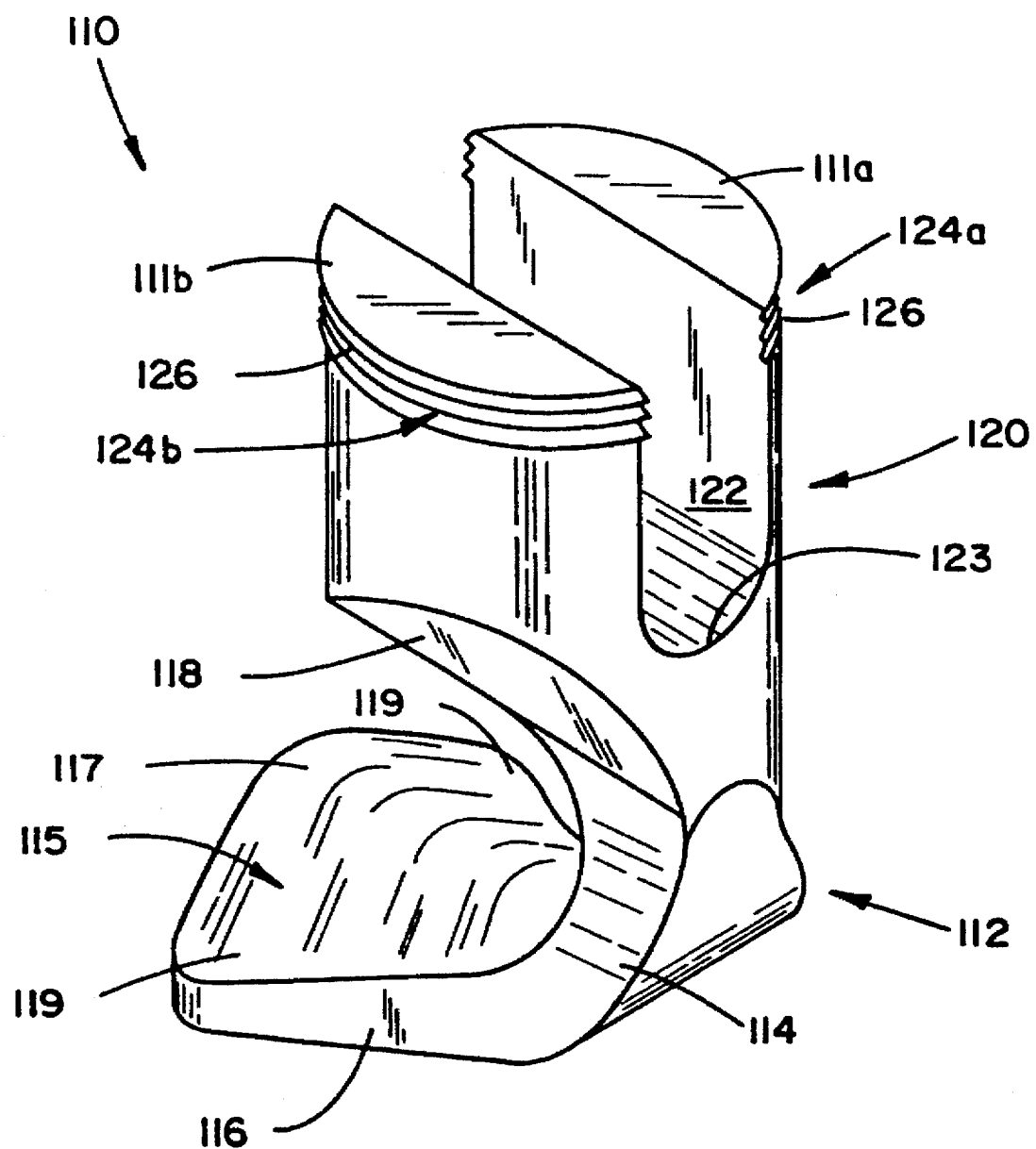
FIGS. 7a and 7b are side perspective views of variations of hook devices of the present invention illustrating the plow and claw variations of the blade portions thereof, respectively.

Referring now to FIG. 7a, the simple plowhook embodiment 110 of the present invention is provided in perspective view. The plowhook 110 comprises a blade 112 and a rod receiving portion 120.

The rod receiving portion 120, which is integrally formed at the top of the blade portion (described more fully hereinafter), comprises a pair of upwardly extending members 111a, 111b, defining therebetween a channel 122 for receiving a support rod therein. The rod receiving channel 122 comprises a curvate lower wall 123 which is ideally suited for receiving a cylindrical rod. The depth of the channel 122 is sufficient such that a cylindrical rod, for example the support rod of the present invention, may be fully inserted thereinto without the rod extending above the height of the upwardly extending members 111a,111b and interfering with the engagement of the rod by external rod securing means. The uppermost portions 124a,124b of the upwardly extending members 111a,111b include a surface threading 126, which is ideally suited for receiving thereon a nut, such as a top locking nut (as described more fully with respect to FIG. 8 et al.)

The blade 112 comprises a C-shaped portion 114 having a lower branch extending member 116, and an upper branch 118 which extends into, and integrally forms the base of the rod receiving portion 120. The lower branch extending member 116 of this embodiment has a curvate conformation, such that it forms an arched surface 115. The arched surface 115 is so formed to be approximately fitted to the arched undersurface of the center of the lamina of the patient's spine. This arched surface 115, therefore, is defined by a surface maximum 117 extending along the center line of the lower branch extending member 116; the surface 115 sloping off to the edges 119 thereof, at an angle which is equal to the approximate angle of the lamina along the underside portions 13a,13b thereof which are adjacent to the centerline undersurface 15.

Figure 7B:
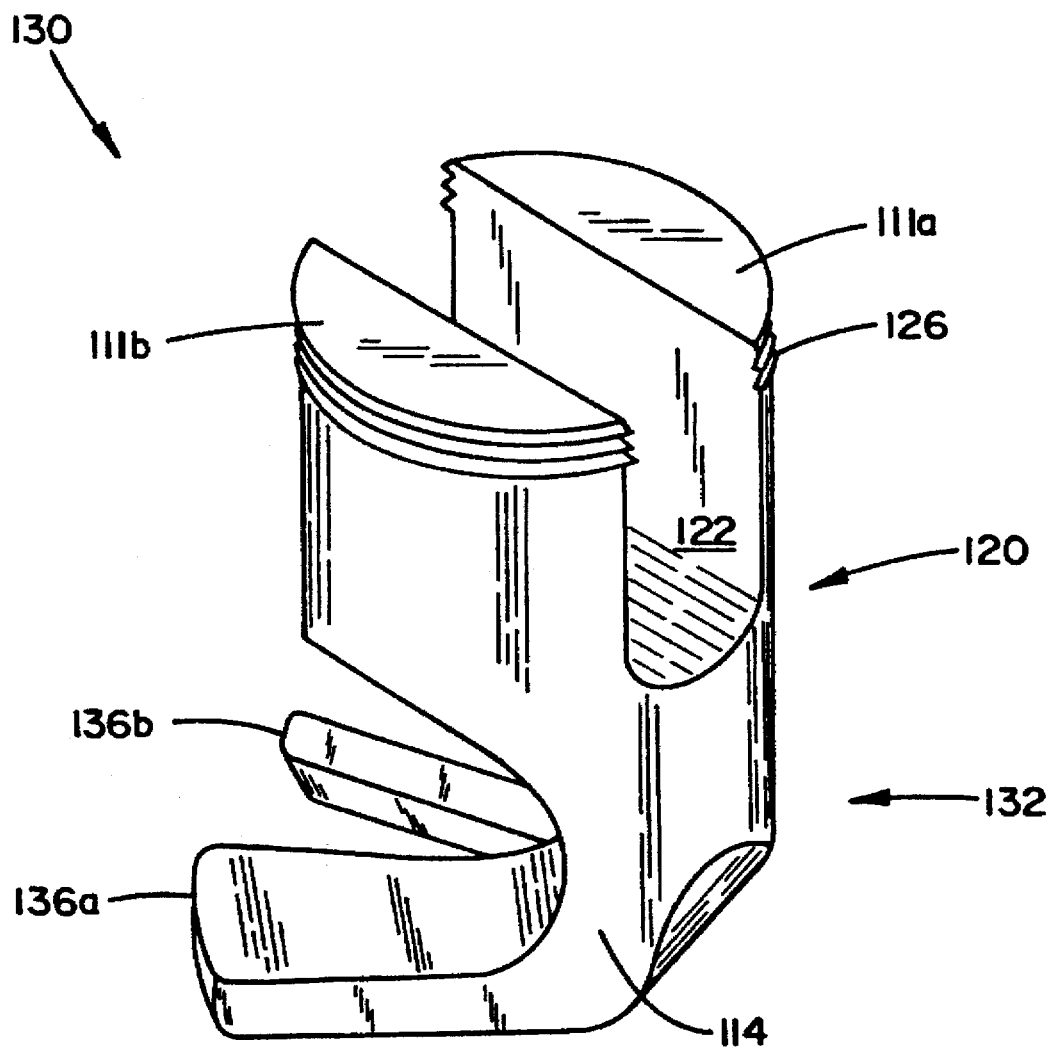

Referring now to FIG. 7b, a second variation 130 of the hook of the present invention is shown, wherein the blade portion 132 comprises a pair of angularly offset extending members 136a,136b which form a claw conformation. The rod receiving upper portion 120 of this simple clawhook embodiment comprise the same features as the plowhook 110 as set forth with respect to FIG. 7a, including upwardly extending members 111a,111b defining a channel 122 for receiving therein a cylindrical support rod, and a threading 126 on the uppermost portion thereof.

As introduced above, the blade portion 132 comprises a pair of extending members 136a,136b. The lower branch of the C-shaped portion 114 is bifurcated so that a pair of angularly offset, but planar, members 136a,136b are produced. Although it is understood that each may have a surface conformation which is more suited to the particular undersurface of the lamina, as shown in FIG. 7b, a substantially flat conformation is sufficient to provide stable and secure seating against the underside of the lamina. More specifically, each of the offset members 136a,136b is ideally suited to being seated against the undersurface of a corresponding portion 13a or 13b thereof which is adjacent to the centerline 15.

Figure 8:
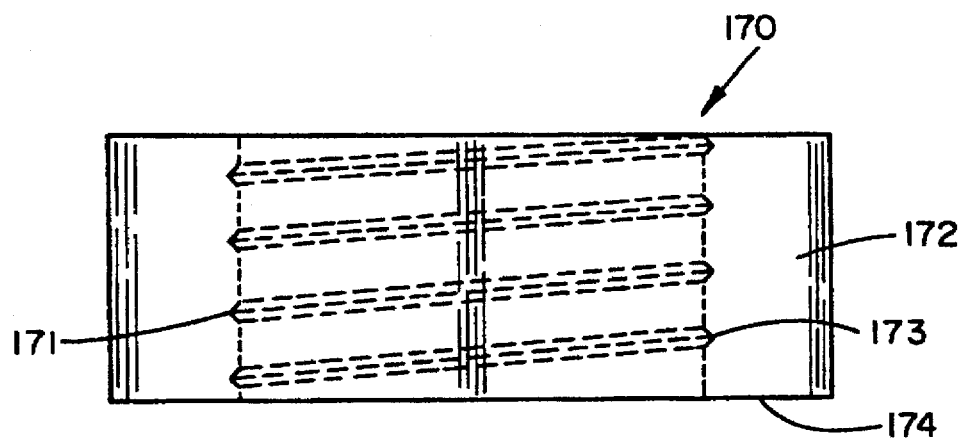
FIG. 8 is a side cross-section view of a top locking nut which is an aspect of the present invention.
Figure 9:
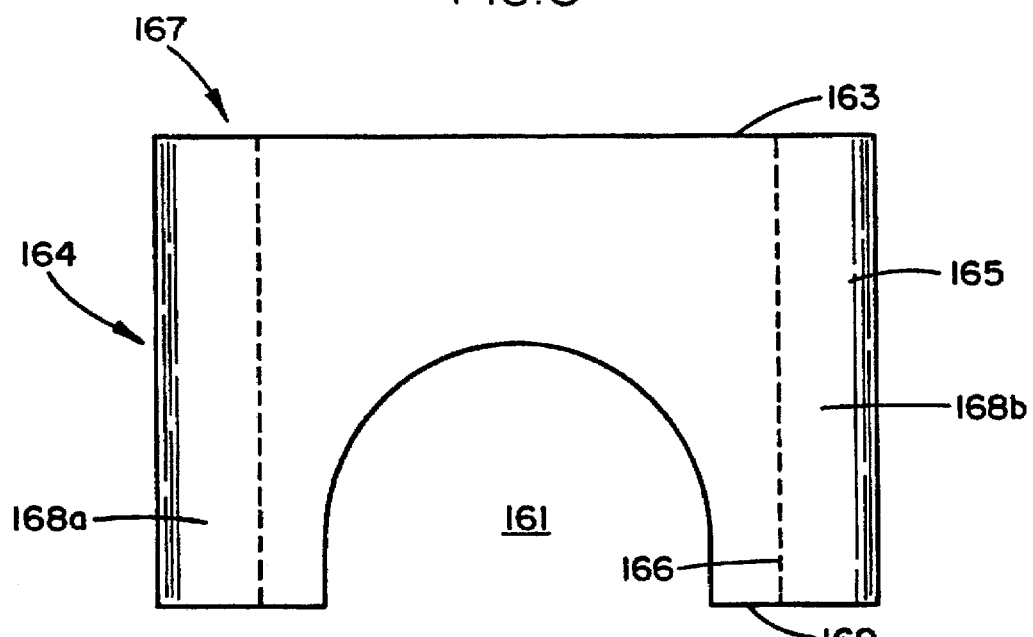
FIG. 9 is a side view of a rod securing sleeve which is an aspect of the present invention.

Referring now to FIGS. 8 and 9, a top locking nut 170 and an optional rod securing sleeve 164 of the first embodiments are shown in side cross-section views. Referring specifically to FIG. 8, the nut 170 comprises an inner threading 171 which is intended to mate with the threading 126 on the uppermost portions 124 of the upwardly extending members 111a,111b of the hook 110 or 130. The bottom surface 174 of the nut 170 is intended to seat against the top surface of the support rod (or the top surface of the rod securing sleeve as set forth with respect to FIG. 9), but is permitted to rotate relative to the rod, therein providing a means for locking the rod in the channel.

Referring now to FIG. 9, the optional rod securing sleeve 164 comprises a hollow cylindrical body having a flat annular top surface 163 and a curved bottom surface 169. In fact, the bottom surface 169 is so curved as to have an upside-down U-shape defined by a pair of downwardly extending members 168a,168b formed of the cylindrical body. These downwardly extending members 168a,168b in turn, define diametrically opposing vertical slots 161, which together provide a passage through the bottom of the sleeve for cupping a rod placed therethrough. The interior surface 166 of the sleeve 164 has a diameter which is equal to the outer diameter of the rod receiving portion 120, so that it may be placed thereover to engage the rod which may be disposed in the channel 122 thereof, and secure same therein.

Figure 10:
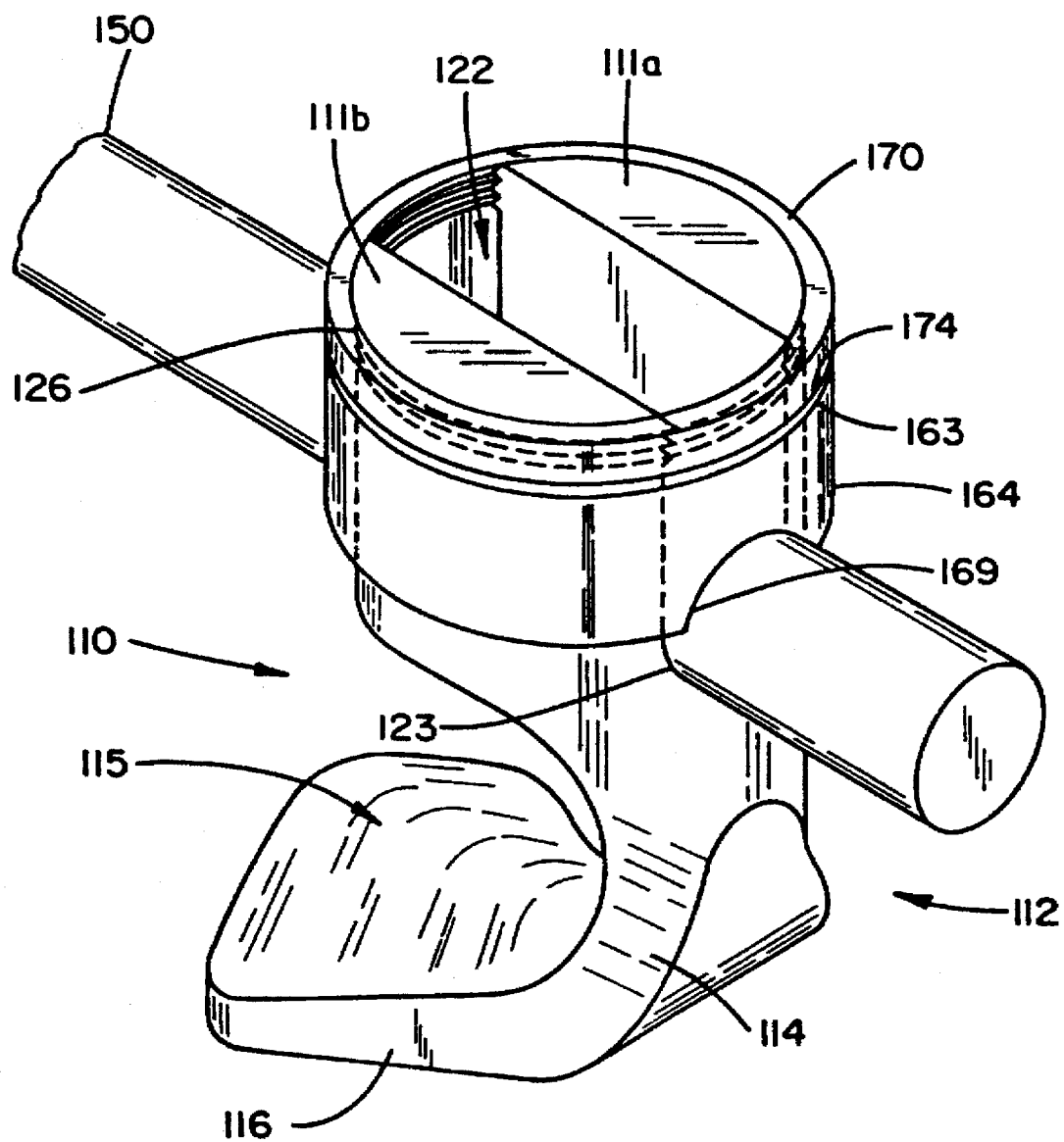

Referring now to FIG. 10, a fully assembled plowhook 110 and attending elements, such as described with respect to FIG. 7a, is provided in perspective view, wherein the support rod 150 of the apparatus is mounted and secured in the channel 122 thereof by means of the optional rod securing sleeve and the top locking nut 170. The implantation procedure which is associated with such an assembly is described hereinalso. It shall further be noted that all alternative embodiments of the rod receiving portions of the present invention are set forth hereinafter and described exclusively with respect to the plow shaped blade originally described with respect to FIG. 7a. All of such rod receiving features, however, are equivalently contemplated in conjunction with the offset bifurcated blade portion as described with respect to FIG. 7b.

More specifically with respect to the assembled hook 110 of FIG. 10, the implantation thereof generally begins with the removal of the spinous process from the upper surfaces of the appropriate lamina. Once these have been removed, the plow shaped extending member 116 is positioned against the lamina such that the C-shaped portion 114 of the blade portion 112 is seated to the lamina and the arched surface 115 of the blade securely engages the arched undersurface 15 of the lamina.

Once a sequence of the hooks 110 are so positioned, the support rod 150 is placed in the channel 122 of the rod receiving body portion 120. The rod securing sleeve 164, as set forth more fully with respect to FIG. 9, may then be dropped over the upwardly extending members 111a,111b such that the curvate undersurface 169 thereof seats against the top of the rod 150, with the U-shaped slots 161 formed thereby receiving therethrough, and securely holding, the rod 150. (It shall be understood that the optional rod securing sleeve 164 may be omitted from the assembled structure, in those variations in which the lower surface 174 of the top locking nut 170 seats against the top of the rod 150.) Subsequent to the disposition of the rod securing sleeve 164 on the body portion 120, the top locking nut 170 is rotationally engaged on the threading 126 of the upwardly extending members 111a,111b such that the bottom annular surface 174 of the nut 170 seats against the top annular surface 163 of the sleeve 164. Continued rotation of the nut 170 so that it descends along the threading 126 causes a downward force to be applied against the sleeve 164, which is in turn applied to the rod 150. The rod is thereby locked in the channel 122 and prevented from both axial, translational, and rotational motion by the engagement thereof between the lower surface 123 of the channel 122 from below, and the curved bottom 169 of the sleeve 164.

Figure 11:
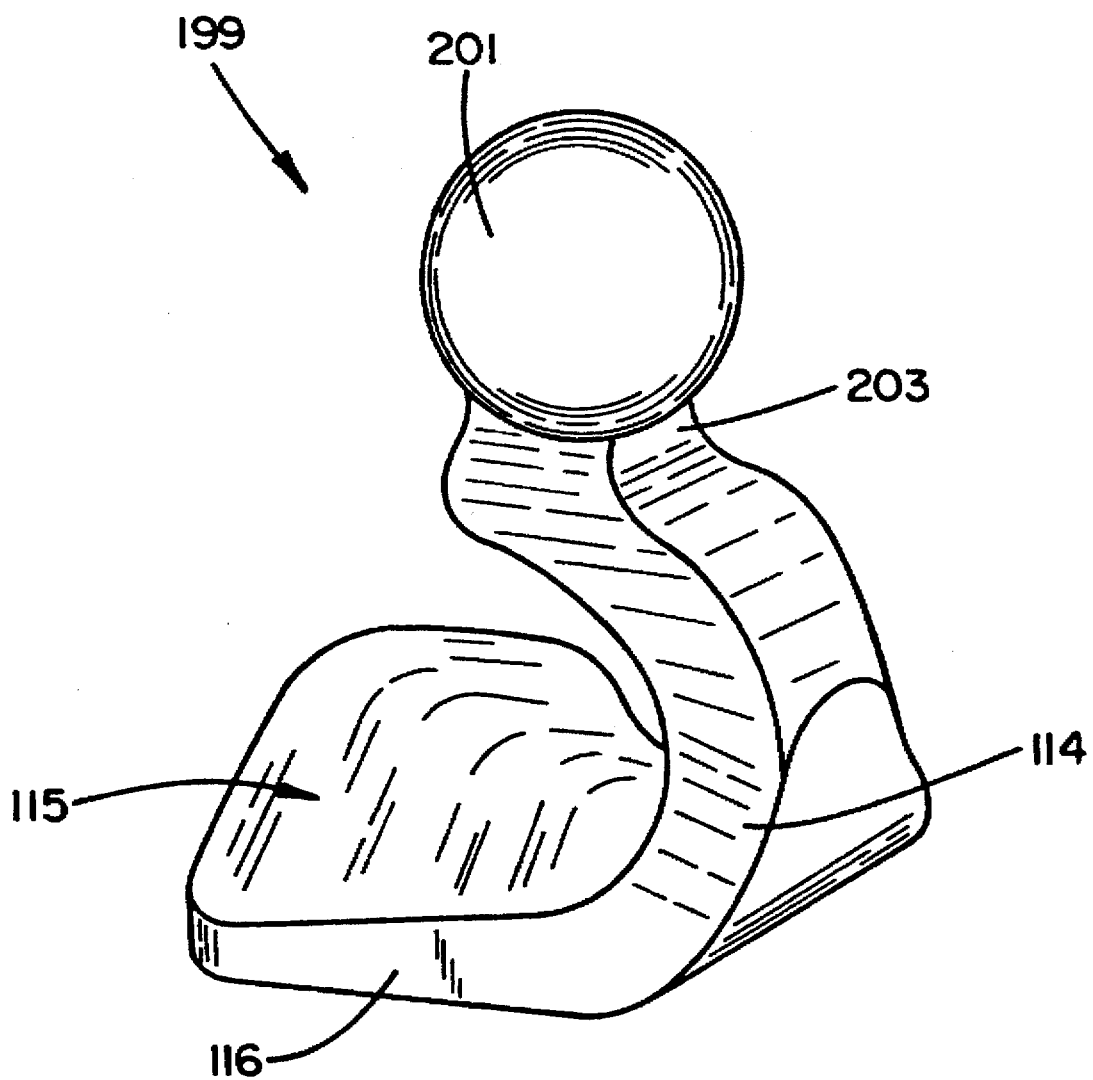
FIG. 11 is side perspective view of a blade portion of a first polyaxial and/or extending embodiment of the hook device of the present invention having a plow conformation.

Referring now to FIG. 11, a side view of the blade portion 199 of the first embodiment of the present invention having a polyaxial and/or extending body is provided. As previously described, this embodiment comprises a plow shaped blade portion, having a lower extending member 116, branching from the lower end of the C-shaped section 114, which has an arched surface 115. In this embodiment, however, a semi-spherical head portion 201 is integrally formed to the end of the upper extending branch of the C-shaped portion 114 at a neck portion 203. It is understood that the semi-spherical shape is a section of a sphere. In the embodiment shown, the section is greater in extent than a hemisphere, and it correspondingly exhibits an external contour which is equidistant from a center point of the head. In a preferred embodiment, the major cross-section of the semi-spherical head 201 includes at least 270 degrees of a circle.

Figure 12:
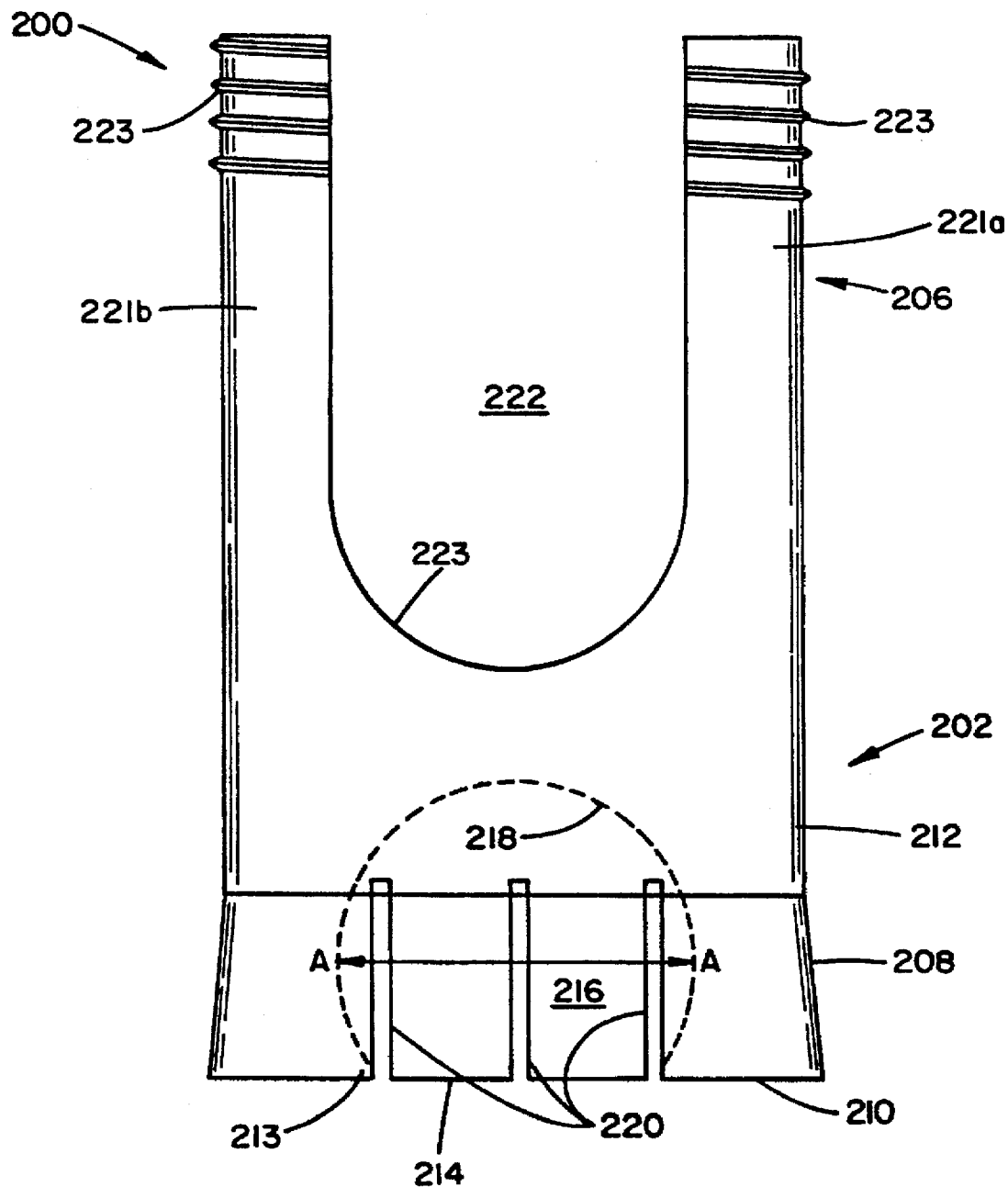
FIG. 12 is a side view of the side loading polyaxial coupling element of the present invention.

Referring now to FIG. 12, a first embodiment of the coupling element 200 of the present invention is shown in a side view, wherein critical features of the interior of the element are shown in phantom. The coupling element 200 comprises a generally cylindrical body which may be conceptually separated into a lower portion 202, and an upper portion 206, each of which shall be described more fully hereinbelow.

First, with respect to the lower portion 202, the exterior surface 208 of the body is tapered in the elongate direction such that the body is wider at the bottom 210 of the lower portion 202 than at the top 212 thereof. The bottom 210 of the element includes an expandable and contractible opening 214, defined by annular lip 213, which forms the mouth of an expandable and contractible interior chamber 216. The diameter of the opening 214, when otherwise unaffected by external deflecting forces, is more narrow than the maximum diameter A—A of the interior chamber 216. The interior chamber 216 has a generally curvate inner surface 218 which is correspondingly shaped to receive the semi-spherical head 201 of the blade portion 199.

The exterior surface of the lower portion 202 includes a series of slots 220 which extend vertically upward from the bottom 210 of the element to a point which is closer to the top 212 of the lower portion 202 than the maximum horizontal diameter A—A of the interior chamber. The slots 220 are provided in order that the application of an external deflecting force may widen or narrow the opening 214 therein permitting the insertion of an object, such as the head 201 of the blade portion, which is larger than the undeflected diameter of the opening 214, or conversely, providing for the retention of an object such as the same.

The upper portion 206 of the generally cylindrical body of the coupling element 200 includes a pair of upwardly extending members 221a,221b which define therebetween a vertical channel 222 in the top of the coupling element 200. The rod receiving channel 222 comprises a curvate bottom 223. As is the case with the first embodiment described with respect to FIGS. 7a and 7b, the depth of the bottom 223 is established such that a circular support rod (see FIG. 15) which is positioned in the rod receiving channel 222 may nests fully within the coupling element 200, and does not extend beyond the vertical extent of the upwardly extending members 221a,221b, which would prevent a top locking nut 170 (or optional rod securing sleeve) from sliding thereover to retain the rod within the channel 222. The vertical extent of the channel 222 is large enough so that the rod may be translated vertically within the channel 222 (the purpose for which is set forth hereinbelow with respect to FIG. 15).

The uppermost portions of the upwardly extending members 221a,221b comprise a threading 223 thereon which is ideally suited for receiving the top locking nut 170 described with respect to FIG. 8.

Figure 13:
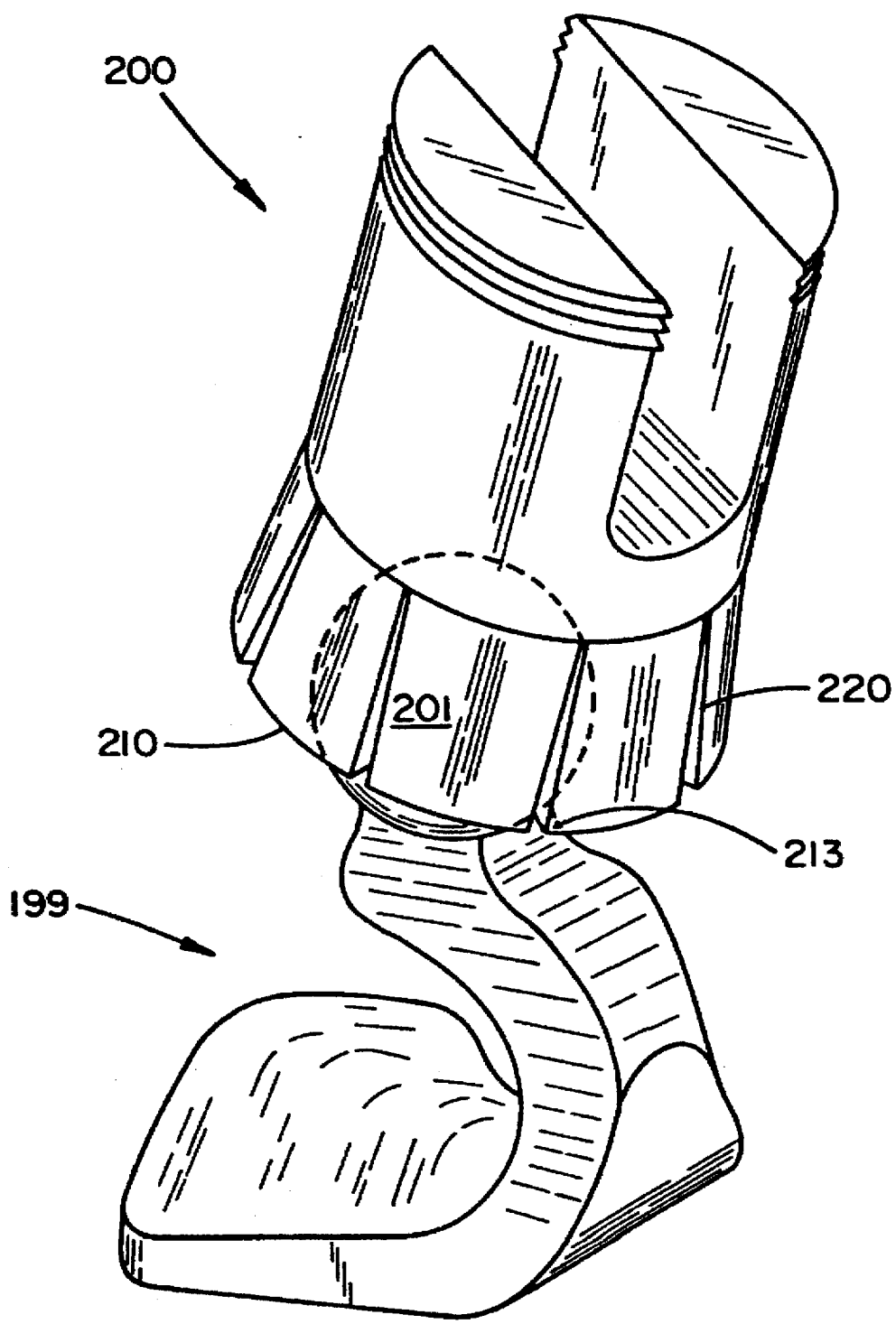
FIG. 13 is a side view of the locking ring which is an aspect of the present invention.

Referring now to FIG. 13, the coupling element 200 and the blade portion 199, as described more fully with respect to FIGS. 11 and 12, are shown in a perspective view, wherein the head 201 of the blade portion 199 has been received within the interior chamber 216, and the head 201 is rotationally free to move relative to the coupling element 200. In this position, however, each is prevented from fully separating from the other by the mutual engagement of the annular lip 213 at the bottom 210 of the lower portion 202 and the diameter of the head 201. The head 201 may be placed in the socket of the coupling element 200 prior to the use by the surgeon in the operating room, or, if desired, the head 201 may be inserted into the socket at the time the surgeon desires it.

Figure 14:
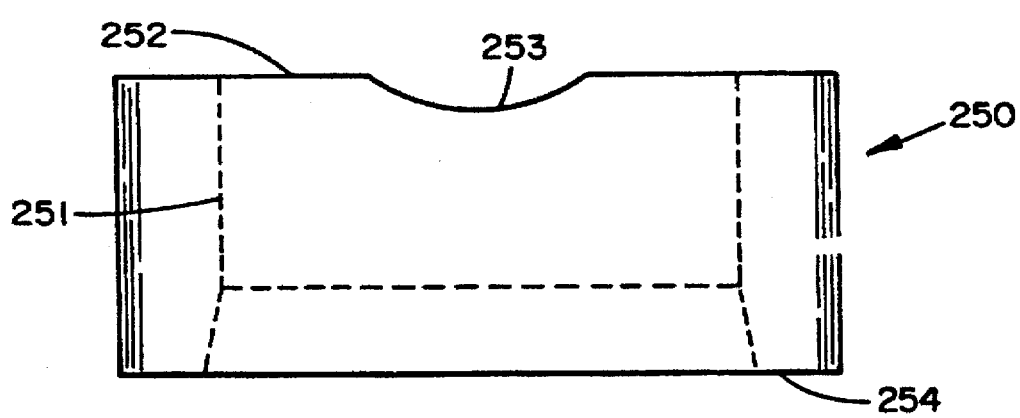
FIG. 14 is a side view of the coupling element of FIG. 12 shown mounted to the semi-spherical ball head of the blade portion as shown in FIG. 11.

Referring now to FIG. 14 the locking ring 250 of the present embodiment is shown in a side view. The locking ring 250 comprises a contiguous annular element having an inner diameter which is equal to the outer diameter of the lower portion 202 at the top 212 thereof. The inner surface 251 of the locking ring may be tapered slightly at the bottom thereof to match the upper portion of the taper of the lower portion 202. In its initial disposition, about the coupling element 200, the ring 250 is positioned so that the upper annular surface 252 thereof is above the bottom 224 of the channel 222. In this disposition, the bottom 254 of the ring 250 extends to a point below the uppermost part 212 of the lower portion 202, the point being determined by the diameters of the tapered lower portion 202 and the tapered inner surface 251 of the ring 250.

The upper surface 252 of the locking ring comprises a notch 253 which is ideally suited and shaped for supporting thereon the rod 150. The locking ring is, therefore, designed to be positioned at the top 212 of the lower portion of the coupling element 200 and for the rod 150 to seat in the notch 253 thereof. Application of pressure downward by the rod causes the ring 250 to crush the inner surface of the interior volume 216 against the semi-spherical head 201.

It shall be understood that a dowel, protuberance, or other suitable means may be provided at or above the top 212 of the lower portion 202 so that the ring 250 may not be easily moved upward, and thereby preventing separation of the locking ring during handling prior to use.

Figure 15:
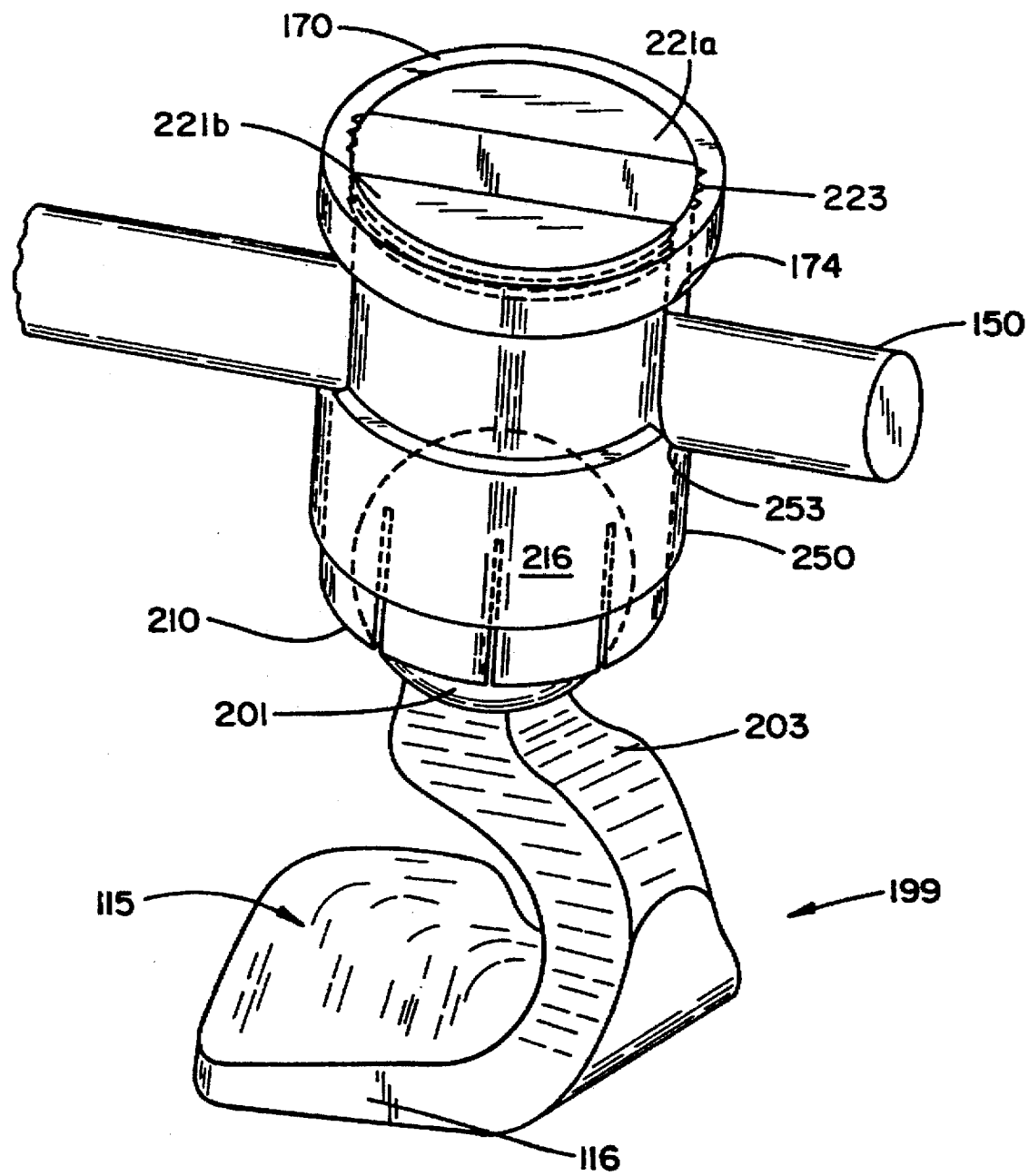
FIG. 15 is a side perspective view of the fully assembled hook of the embodiment of the present invention as shown in FIG. 14.

With reference now to FIG. 15, which shows a side perspective view of the fully locked coupling element, rod, and plow hook system, the preferred method of implantation and assembly is described hereinbelow. As with the previous embodiments, the lower extending member 116, and the arched surface 115 thereof, is positioned under the arched underportion of the lamina. The head 201 of the blade portion 199 is then inserted into the interior chamber 216 of the coupling element 200. (As stated above, as well, this step may, of course, be taken prior to the positioning of the blade portion relative to the lamina.) At this point in the assembly process, the locking ring 250 has been positioned about, but not yet forced downward along, the outwardly tapered lower portion 202, so that the coupling element 200 may still rotate and angulate relative to the positioned blade portion 199.

At this stage of the assembly, support rod 150 is positioned in the channel 222 and the top locking nut 170 is introduced on the threading 223 of the upwardly extending members 221a,221b. (In the optional variation, the rod securing sleeve 164 is placed between the rod 150 and the top locking nut 170 in order that the rod 150 extends through the slots 161 defined in the curved bottom surface 169 thereof.) The rod 150 is prevented from fully descending into the channel 222 by the top surface of the locking ring 250.

Once the proper angulation of the coupling element 200 to the blade portion 199, and the secure nesting of the rod 150 within the receiving channel 222, have been established, the top locking nut 170 is tightened down onto the rod 150. The lower surface 174 of the nut 170 seats against the top surface of the rod. As the nut 170 rotates, and descends along the threading 223 relative to the coupling element, the support rod 150 is forced to translate downward in the channel 222, causing the locking ring 250 to translate downward along the lower portion 202 of the coupling element 200. By descending along the tapered lower portion 202 of the element, the locking ring 250 provides an inwardly directed deflecting force which causes the slots 220 in the lower portion 202 of the element to narrow so that the ring may proceed downward. This deflection inward causes the inner surface 218 of the interior chamber 216 to crush lock against the head 201 of the blade portion 100. This clamping force locks the angulation of the coupling element 200 relative to the blade portion 199. Ultimately, once the locking ring 250 cannot be translated down any further, the downward force of the nut 170 against the rod 150 causes it to be fully locked between the top locking nut 170 and the top surface of the locking ring 253. The full insertion of the top locking nut 170, therefore, locks the rod 150 to the coupling element 200, as well as the blade portion 199 to the coupling element 200.

Figure 16:
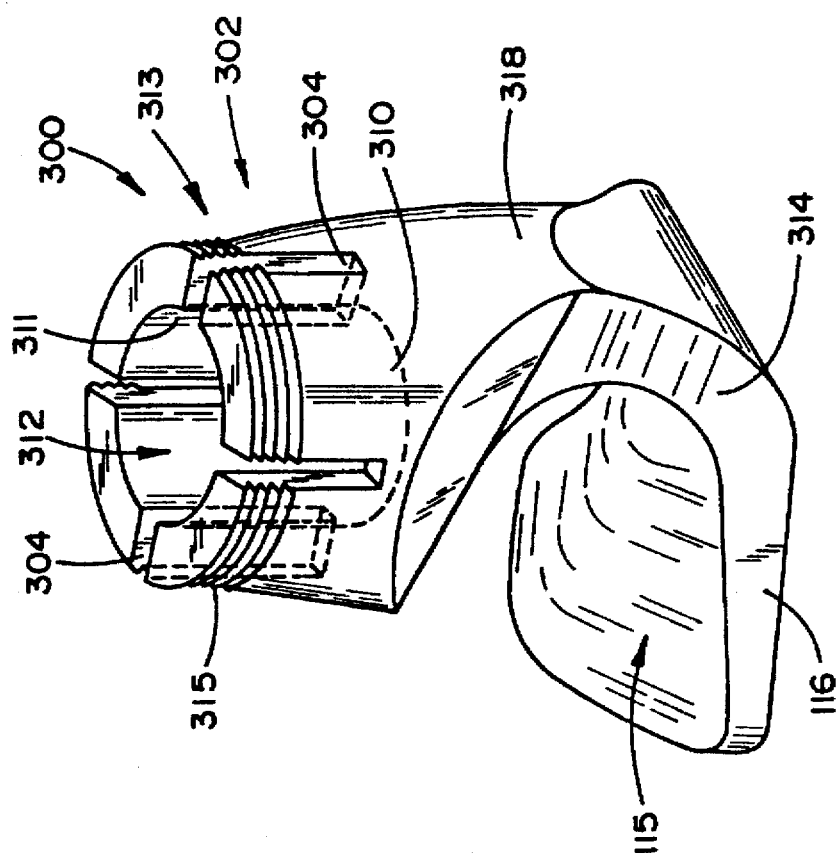
FIG. 16 is a side perspective view of the blade portion of an other embodiment of the present invention having a contractible cylindrical recess therein.

Referring now to FIG. 16, the blade portion 300 of the third embodiment of the present invention is shown wherein it comprises a body receiving portion 302 and a C-shaped portion 314. As in the above described embodiments, the lower extending branch of the C-shaped portion 314 comprises an extending member 116 which has an arched surface 115 which is understood to be the portion which is inserted under the center of the lamina of the patient's spine. The body receiving portion 302 is positioned at the upper extending branch of the C-shaped portion 314 at the end 318 thereof.

The body receiving portion 302 comprises a cylindrically shaped recess 310 being defined by an inner tubular surface 311. The axis of the cylindrical recess 310 is oriented to be generally perpendicular to the axis of the spine, and transverse to the axis of the support rod of the implant apparatus. The top of the cylindrically shaped recess 310 comprises an opening 312 defined by the upper annular portion of the inner surface 311 and an outer annular surface 313. The opening further includes slots 304 so that the opening may be selectively narrowed by an inwardly directed radial force. The outer surface 313 of this opening 312 is tapered such that it widens as a function of distance from the opening. This tapered outer surface 313 further comprises an external threading 315 so that a nut may be introduced thereonto; the downward translation of which provides an inward radial force to contract the opening 312 of the cylindrical recess 310.

Figure 17:
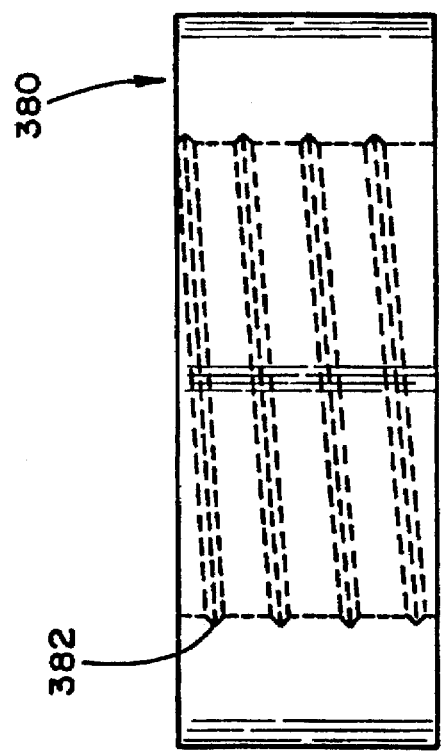
FIG. 17 is a side cross-section view of a tightening nut which is an aspect of the present invention.

Referring now to FIG. 17, the tightening nut 380 comprises an interior threading 382 which is designed to engage the outer upper surface 313 of the recess 310 and be rotationally translated downward on the threading 315 thereof. This downward translation causes the nut 380 to apply the inwardly directed radial force necessary for the slots 314 to be closed, thereby narrowing the opening 312 and crush locking the inner surface 311 of the opening against any properly fitted cylindrically shaped object which may be placed therein and thereby locking it within the recess 310.

Figure 18:
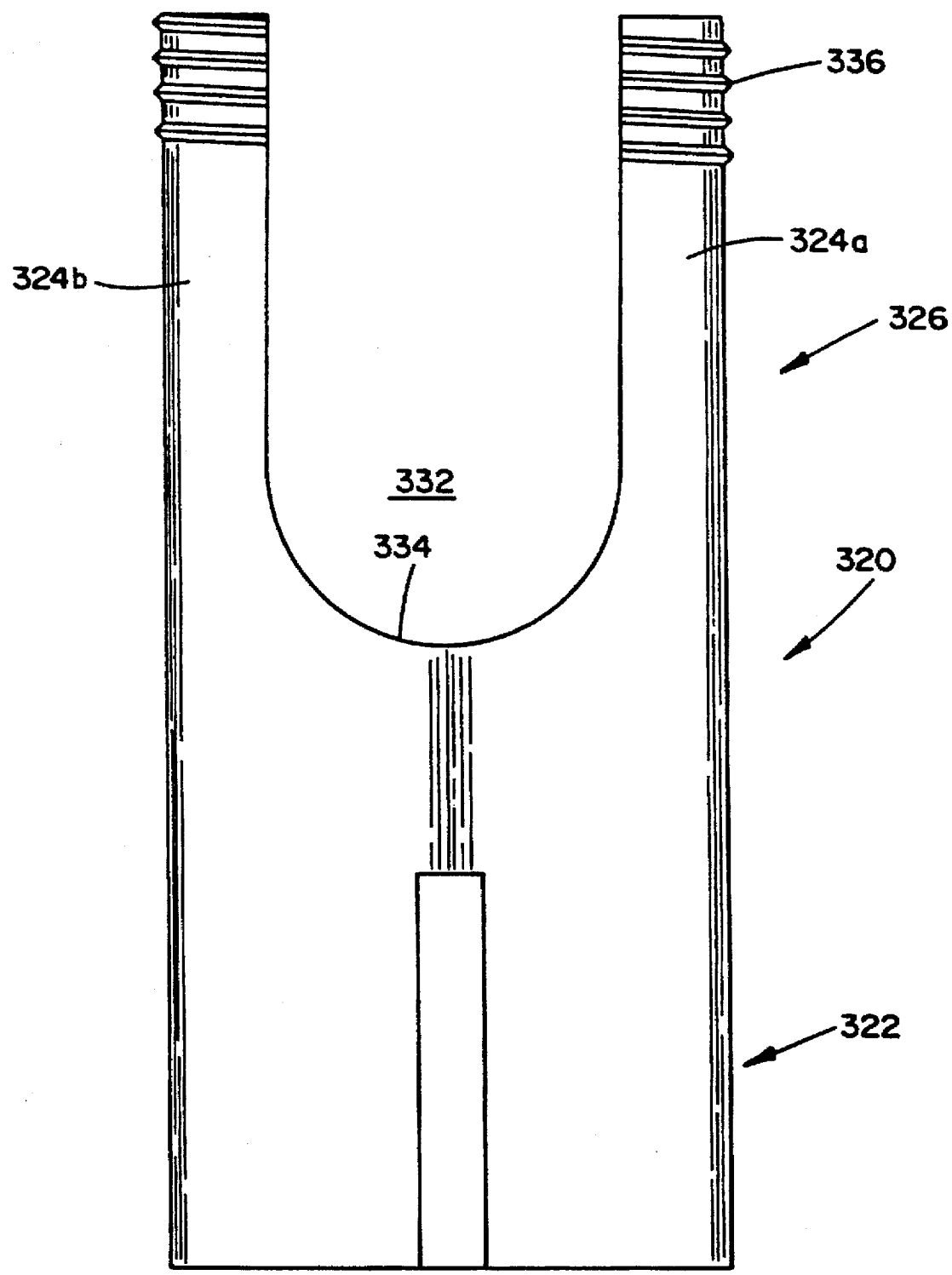
FIG. 18 is a side view of the body portion which is an aspect of the embodiments of the present invention of which the blade portion of FIG. 16 is also an aspect.

Referring now to FIG. 18, the body portion 320 of the third embodiment of the present invention, which is to be engaged by and mounted in the recess 310 of blade portion 300 is shown in a side view. The body 320 comprises a generally cylindrical shape which may be conceptually separated into a shaft portion 322 and an upper portion 326, each of which shall be described more fully hereinbelow.

First, with respect to the shaft portion 322, the body portion 320 is designed to be slidably mounted in the cylindrical recess 310 of the blade portion 310 (see FIG. 16) and as such has a generally cylindrical shape. This shaft 322 must be long enough to provide a sufficiently large stroke within the recess 310 so that the height of the upper portion 326 of the body 320 may be varied enough to compensate for misalignments of the support rod relative to the entire assembly. The shaft 322 is cylindrical in shape for the additional purpose of permitting the body 320 to be rotated within the recess 310, so that the rod receiving means, as described more fully hereinbelow with respect to the upper portion, may be positioned to receive the rod independent of normal deviations from the standard axial disposition of the rod.

The upper portion 324 of the generally cylindrical body 320 is similar to the equivalent portions of the coupling element 200 shown in FIGS. 12, 13, and 15 as well as the rod receiving portions of FIGS. 7a and 7b, and therefore includes a pair of upwardly extending members 324a,324b defining therebetween a channel 332 in the side thereof. The rod receiving channel 332 comprises a curvate bottom 334. The depth of the bottom 334 is established such that a circular support rod (see FIG. 19) which is positioned in the channel 332 may nests fully within the body 320, and does not extend above the extent of the upwardly extending members 324a,324b, which would prevent a top locking nut 170 (or optional rod securing sleeve 164) from sliding thereover to retain the rod within the channel 332. The radius of curvature of the bottom 334 is ideally matched to the radius of the support rod so that the rod is rigidly held in the channel 332, and cannot move vertically once positioned therein.

Figure 19:
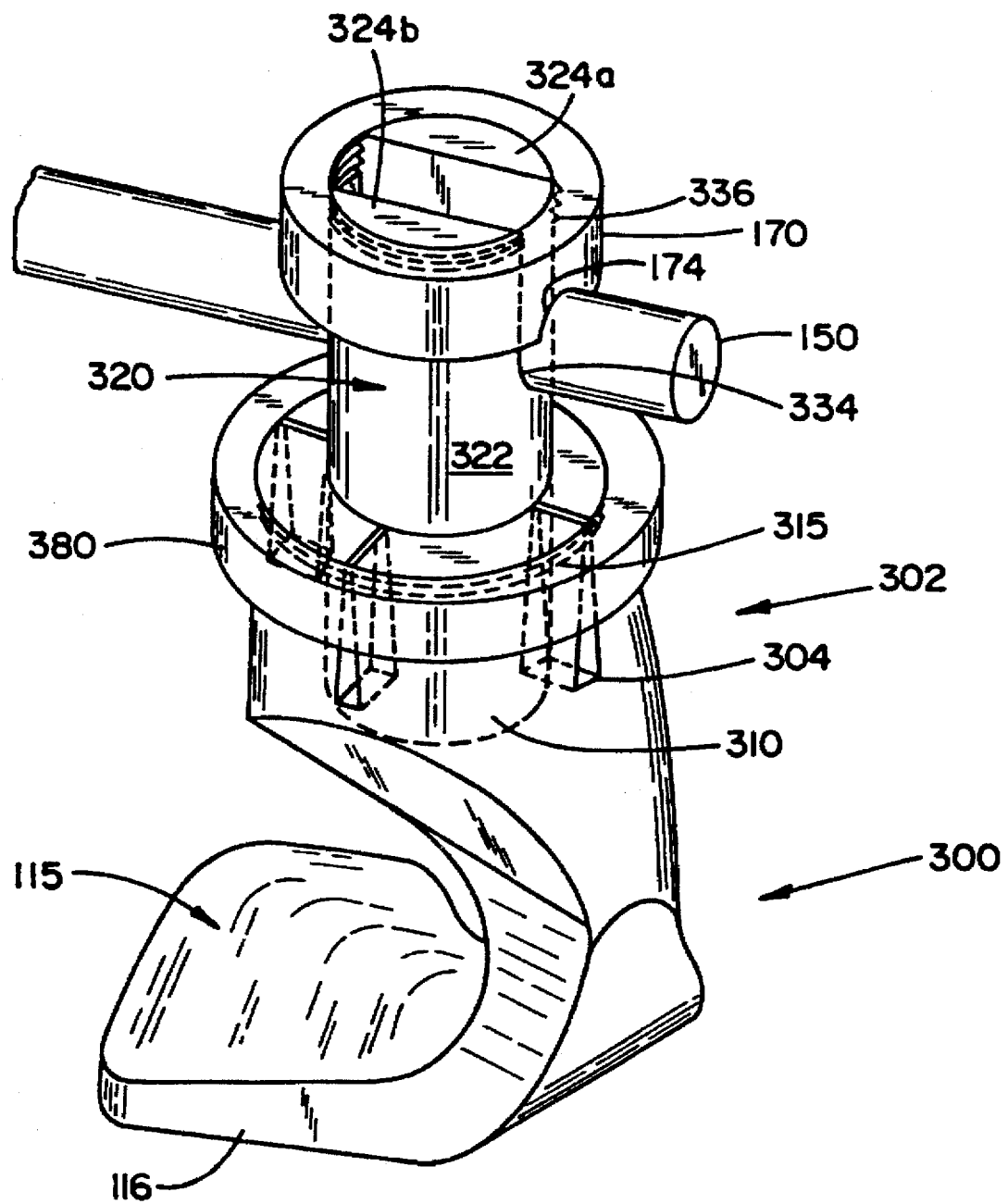
FIG. 19 is a side perspective view of a fully assembled hook device of the present invention, wherein the blade element of FIG. 16 and the body element of FIG. 18 are utilized.

The uppermost portions of the upwardly extending members 324a,324b comprises a threading 336 thereon, which is ideally suited for receiving a top locking nut (see FIG. 19).

With reference now to FIG. 19, which illustrates the fully assembled hook device of this third embodiment, including the support rod 150, a step by step method of implantation is described, wherein each element set forth with respect to FIGS. 8, 14, and 16–18 is utilized. (It is understood that a variation may be assembled in which the optional rod securing sleeve 164 is positioned between the locking nut 170 and the rod 150.) As with the previous embodiments, first the blade portion 300 is mounted to the lamina, such that the flat extending member 116 thereof is disposed beneath the lamina and the body receiving portion 302 is disposed above the lamina. The shaft portion 322 of the body 320 is then positioned in the cylindrical recess 310 at the proper height and rotational orientation. It may be desirable for the shaft to be coupled within the recess 310 so that it may not be fully removed therefrom, but may be raised and rotated as necessary.

Once properly set the tightening nut 380 is introduced onto the threading 315 of the blade portion 300. It is understood that the tightening nut 380 may have been placed on the outer tapered surface 313 prior to the introduction of the shaft 322 in the recess 310, or the tightening nut may be dropped over the body 300 to engage the threading 315. Tightening of the nut 380 on the outer threading causes the nut 380 to translate downward on the outer tapered surface 313, thereby applying an inward force against it, and closing the slots 304. The inner surface 311 of the recess 310 is then locked to the shaft 322 preventing further movement thereof relative to the blade portion 300.

Once the shaft portion 322 is locked in position, the support rod 150 may be positioned between the upwardly extending members 324a,324b, in the channel 332. The top locking nut 170 is then threadably mated to the threading 336 of the upper portion 326, the downward translation of which causes the bottom surface 174 of the nut 170 to seat against the top surface of the rod. The nut 170, thereby, supplies the necessary force to hold the rod securely in the channel 322, locking the rod against the bottom 334.

Figure 20:
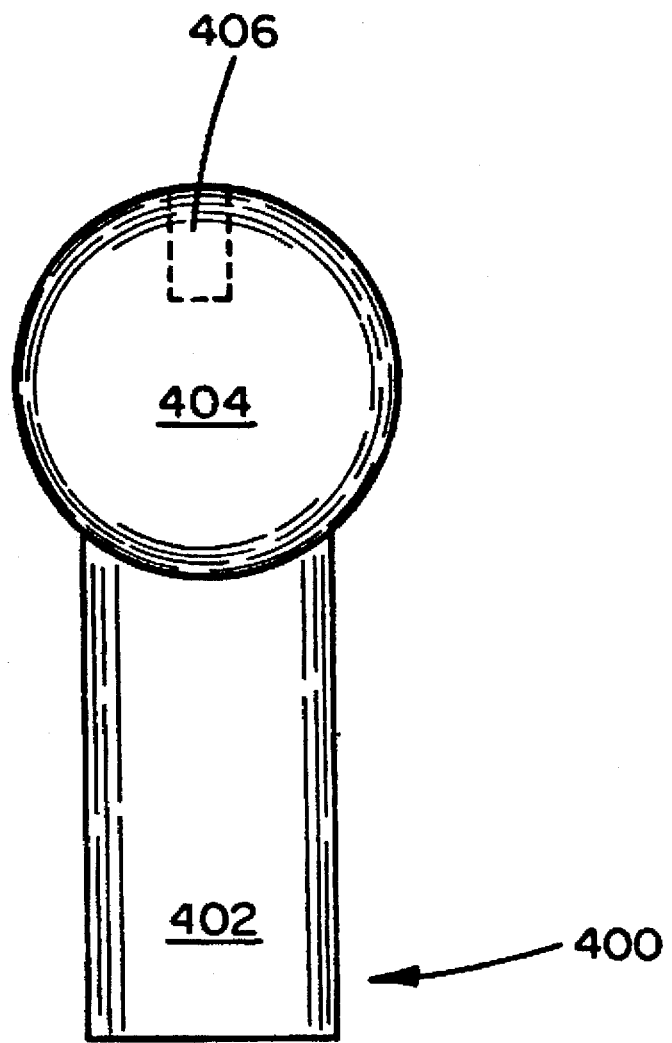
FIG. 20 is a side view of a body portion of an aspect of the present invention, wherein the body portion includes a semi-spherical head.

Referring now to FIG. 20, the body portion 400 of the fourth variation of the present invention, wherein the rod receiving portion of the hook device comprises the coupling element 200 as described hereinabove with respect to FIG. 12, so that the rod receiving channel 222 may be angulated relative to the blade portion 300 (and the body portion 400), is shown. The body comprises a shaft portion 402, which is similar in all respects to the shaft portion 322 of the body 320 of the previous embodiment. In addition, however, the body 400 has only a semi-spherical head 404 at the distal end of the shaft 402. This semi-spherical head 404 further comprises a recess 406 in the top thereof for coupling to a post (not shown) so that the surgeon using the present device may raise and lower the body portion 400 relative to the blade portion 300 more easily. It is preferable that this recess 406 be threaded so that the post may engage the head 404 via a threaded end.

Figure 21:
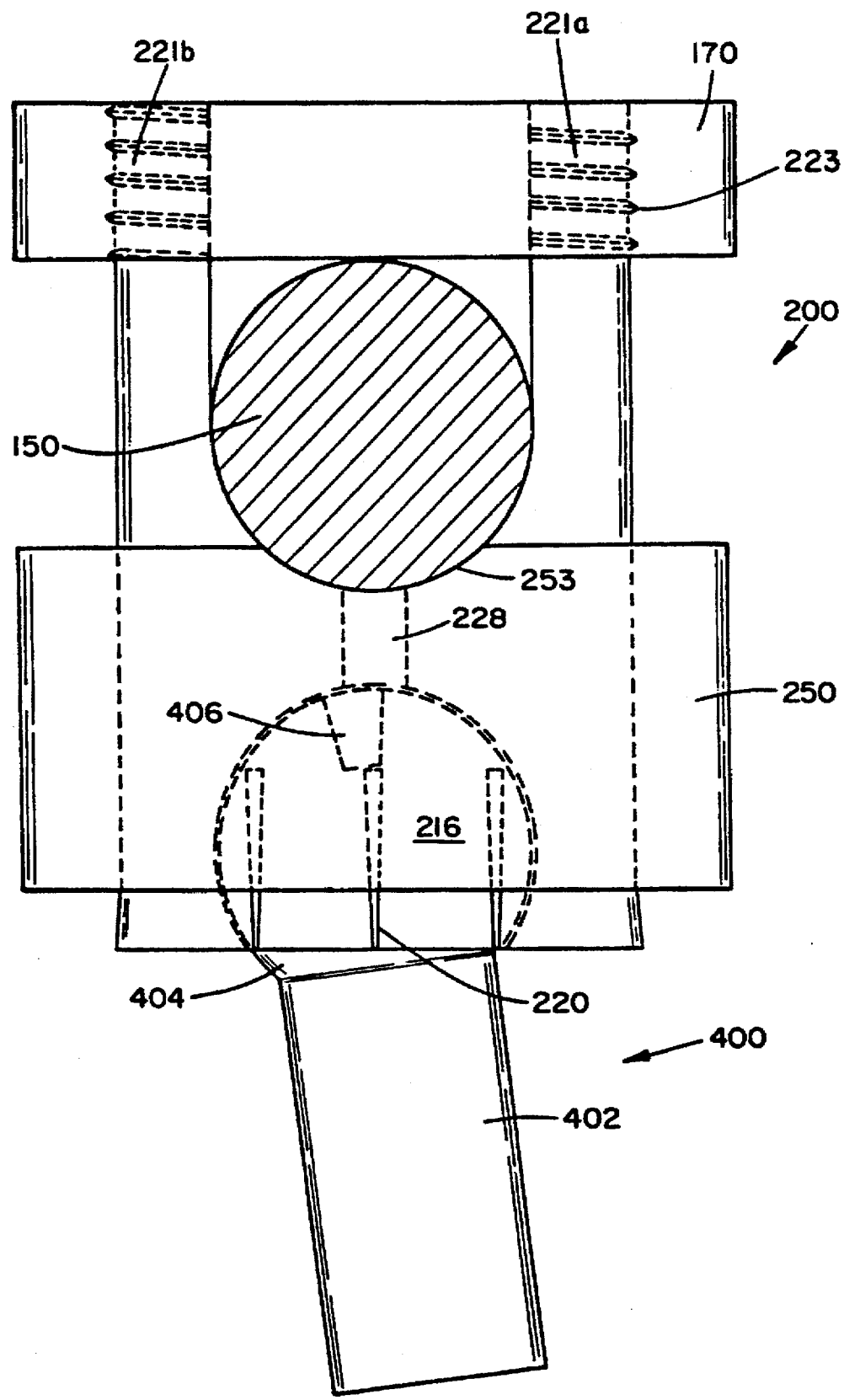
FIG. 21 is a side view of a fully assembled embodiment of the body portion of an aspect of the present invention, wherein the semi-spherical head portion is received in the socket portion of the coupling element of FIG. 12.

With reference now to FIG. 21, which shows a side view of the coupling element 200 locked to the semi-spherical head 404 of the body portion 400, the preferred method of implantation and assembly is described hereinbelow. First, the blade portion 300 is positioned on the lamina (not shown) such that the extending member 116 thereof is positioned under the lamina and in the spinal canal. It is critical that the arched surface 115 be positioned as close to flush against the arched underside of the center of the lamina as possible. Then the body portion 400 is locked in place relative to the blade 300, in a manner identical to the way described with respect to each of the previously described embodiment; the tightening nut 380 being used to crush lock the cylindrical recess 310 of the blade portion 300 to the shaft portion 322 of the body 320.

Once the body is rigidly positioned relative to the lamina, the head 404 thereof is inserted into the interior chamber 216 of the coupling element 200. (This step may, of course, be taken prior to the locking of the shaft 402 to the blade portion 300, however, in such a case, the surgeon may need to rotate the polyaxial coupling element such that a threaded post may be inserted down the axial passageway 228 of the coupling element 200, into the interior chamber 216, and couple with the recess 406 in the semi-spherical head 404, so that the shaft 402 may be raised and lowered relative to the blade portion 300 to attain the proper height adjustment.)

At this point in the assembly process, the locking ring 250 has not yet been forced downward along the outwardly tapered lower portion 202, thereby providing the coupling element 200 with the capacity to rotate and angulate relative to the shaft 402 (and the blade portion 300). This permits the support rod 150 to be properly nested within the rod receiving channel 222 in spite of small misalignments of the rod. After the rod 150 is appropriately positioned, the top locking nut 170 (and optionally the rod securing sleeve 164) is threadably engaged on the threading 223 of the upwardly extending members 221a,221b. Once the proper angulation of the coupling element to the body 400, and the secure nesting of the rod 150 within the receiving channel 222, have been established, the top locking nut 170 (as shown in FIG. 8) is fully tightened such that the lower surface 174 of the nut 170 seats against the top surface of the rod 150 and causes it to descends. This motion forces the support rod 150 to translate downward in the channel 222, causing the locking ring 250 to translate downward along the lower portion 202 of the coupling element 200. By descending along the tapered lower portion 202 of the element, the locking ring 250 provides an inwardly directed deflecting force which causes the slots 220 in the lower portion 202 of the element to narrow so that the ring may proceed downward. This deflection inward causes the inner surface 218 of the interior chamber 216 to crush lock against the head 404 of the body 400. This clamping force locks the angulation of the coupling element 200 relative to the body 400. Ultimately, once the locking ring 250 cannot be translated down any further, the downward force of the nut 170 against the rod 150 causes it to be locked between the nut 170 and the top surface of the locking ring 250. This locking prevents the rod 150 from sliding relative to the assembled structure. The full insertion of the top locking nut 170, therefore, locks the rod 150 to the coupling element 200, as well as the body 400 to the coupling element 200.

Figure 22:
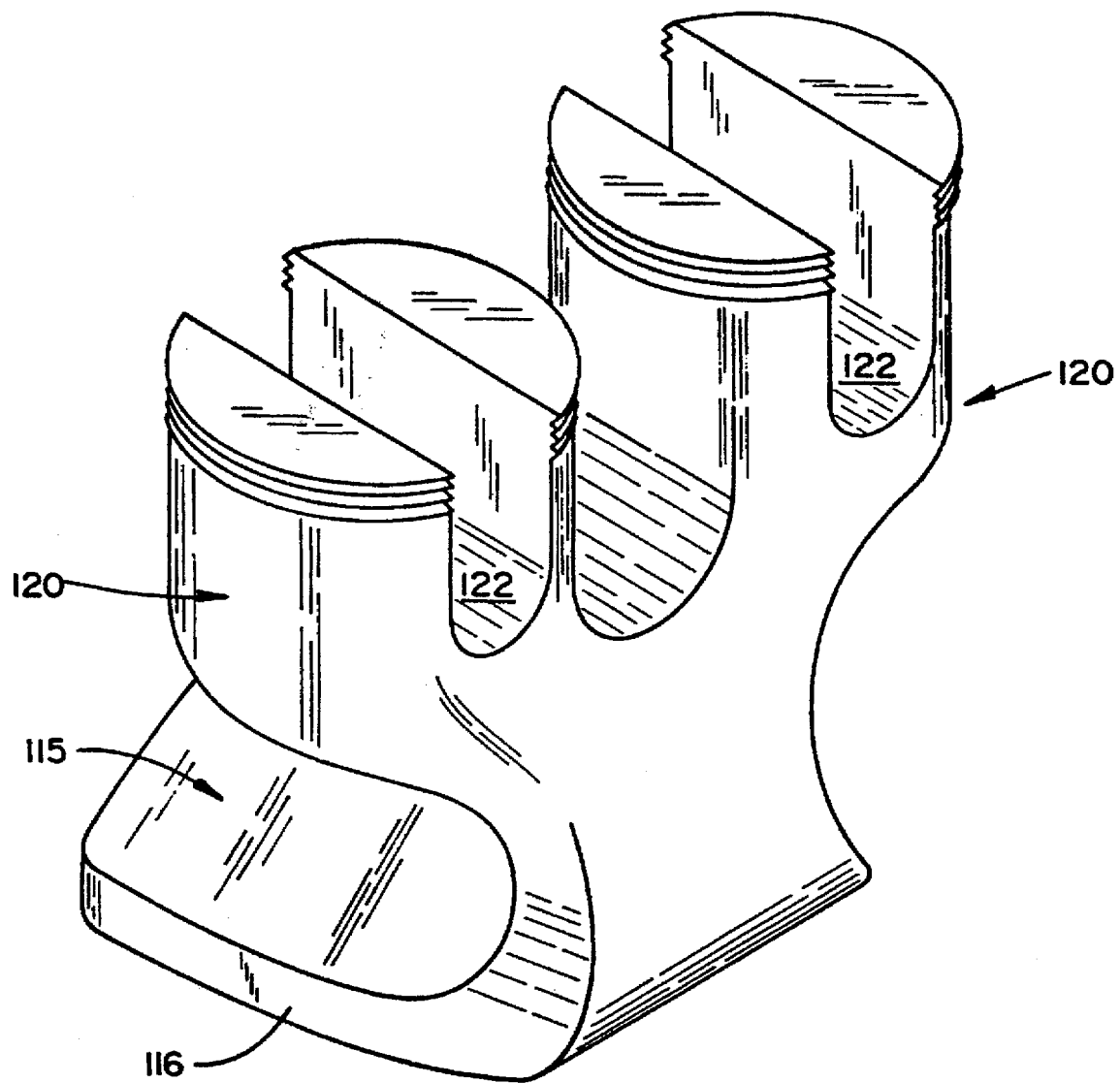
FIG. 22 is a side perspective view of a hook device of the present invention wherein the blade portion is a plow shape and there are a pair of rod receiving bodies extending upwardly and outwardly from the top of the blade portion.

Referring now to FIG. 22, an alternate variation of the first embodiment, originally set forth with respect to FIG. 7a, is shown wherein the rod receiving portion comprises a pair of cylindrical body portions 120, each having pairs of upwardly extending members defining respective channels 122 therebetween for receiving a support rod. In such a conformation, it is possible for the surgeon to not resect the spinous process, however, such a device would be primarily useful in providing a second rod alignment axis of channels by which a de-curving force may be applied to the spine prior to final fixation via the first axis of channels.

While there have been described and illustrated a variety of embodiments of a single rod and hook apparatus which is provided for immobilization of the spine via fixation of specifically formed hooks, both plow and claw shaped, to the arched portion of the lamina; as well as a variety of different hooks having polyaxial and or extending rod receiving portions, it will be apparent to those skilled in the art that further variations and modifications are possible without deviating from the broad spirit and principle of the present invention. The present invention shall, therefore, be limited solely by the scope of the claims appended hereto.

We claim:

1. An orthopaedic hook and rod apparatus, comprising:
    a support rod defining a longitudinal axis;
    at least one blade element, including
        a curved section conformally shaped to nest against a lateral surface of a human lamina along a central vertical axis thereof,
        a lower extending member having an arched upper surface defining a surface maximum which extends along a line which is coplanar with said longitudinal axis defined by the support rod, which arched upper surface is thereby conformally shaped to nest against an arched undersurface of the human lamina at the central vertical axis thereof, and
        an upper portion which is positionable above the human lamina along the central vertical axis thereof,
    said upper portion including at least one channel therein for receiving said support rod; and
    means for locking said support rod in said at least one channel.

2. The apparatus as set forth in claim 1 wherein said body portion further includes at least one surface threading disposed on an outer surface thereof, and wherein the means for locking the support rod in said at least one channel comprises at least one corresponding top locking nut, mateable with said surface threading.

3. The apparatus as set forth in claim 1, wherein said upper section comprises a pair of upwardly extending members, each including a channel therein.

4. An orthopaedic hook for use with central vertical axis orthopaedic rod implantation apparatus, comprising:
    a blade portion, including
        a curved section which is nestable against the lateral surface of a human lamina at the central vertical axis thereof, a lower extending member, and
        an upper section which is positionable above the lamina along the central axis thereof, said upper section including at least one channel for receiving therein a support rod, said at least one channel defining a longitudinal axis,
    said lower extending member having an arched upper surface defining a surface maximum which extends along a line which is coplanar with said longitudinal axis defined by the support rod, and
    means for locking said at least one channel in said at least one channel.

5. The apparatus as set forth in claim 4, wherein said upper section further includes a surface threading disposed on at least one outer surface thereof, and wherein the means for locking the support rod in said at least one channel comprises at least one corresponding top locking nut, mateable with said at least one surface threading.

6. The apparatus as set forth in claim 4, wherein said upper section comprises a pair of upwardly extending members, each including a channel therein.

* * * * *